United States Patent
Roh et al.

(10) Patent No.: US 10,647,685 B2
(45) Date of Patent: May 12, 2020

(54) ANTI-INFLAMMATORY 6-PHENOXYPYRIMIDINE DERIVATIVES, PROCESS FOR THEIR PREPARATION AND PHARMACEUTICAL COMPOSITION CONTAINING THEM

(71) Applicant: Korea Institute of Science and Technology, Seoul (KR)

(72) Inventors: Eun Joo Roh, Seoul (KR); Karam Mohamed Hasan Fara Ahmed, Seoul (KR); So Ra Paik, Seoul (KR); Woo Young Hur, Seoul (KR); Elkamhawy Ahmed, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 16/015,596

(22) Filed: Jun. 22, 2018

(65) Prior Publication Data

US 2018/0370922 A1 Dec. 27, 2018

(30) Foreign Application Priority Data

Jun. 23, 2017 (KR) .................. 10-2017-0079664

(51) Int. Cl.
| | | |
|---|---|---|
| *C07D 239/48* | (2006.01) | |
| *A61P 1/00* | (2006.01) | |
| *A61P 19/02* | (2006.01) | |
| *C07D 413/12* | (2006.01) | |

(52) U.S. Cl.
CPC .............. *C07D 239/48* (2013.01); *A61P 1/00* (2018.01); *A61P 19/02* (2018.01); *C07D 413/12* (2013.01)

(58) Field of Classification Search
None
See application file for complete search history.

(56) References Cited

U.S. PATENT DOCUMENTS

| | | | |
|---|---|---|---|
| 7,504,396 B2 * | 3/2009 | Nunes ................. | C07D 213/82 514/235.8 |
| 8,729,091 B2 | 5/2014 | Bissantz et al. | |
| 8,895,573 B2 | 11/2014 | Coats et al. | |
| 9,375,431 B2 | 6/2016 | Lee et al. | |

FOREIGN PATENT DOCUMENTS

| | | |
|---|---|---|
| EP | 1185525 B1 | 2/2007 |
| WO | WO 2005/037800 A1 | 4/2005 |
| WO | WO 2009/145856 A1 | 12/2009 |

OTHER PUBLICATIONS

Farag et al., European Journal of Medicinal Chemistry, vol. 141 (2017), pp. 657-675.*
Miyasaka, Nobuyuki, et al., "Nitric Oxide and Infammatory Arthritides". Life Sciences, 1997, vol. 61, No. 21, pp. 2073-2081.
Jang, Daniel, et al., "Nitric Oxide in Arthritis", Free Radical Biology & Medicine, 1998, vol. 24, No. 9, pp. 1511-1519.
Kopecky, David J., et al., "Identification and Optimization of N3,N6-diaryl-1H-pyrazolo[3,4-d] pyrimidine-3,6-diamines as a novel class of ACK1 inhibitors", *Bioorganic & Medicinal Chemistry Letters*, Nov. 1, 2008, vol. 18, pp. 6352-6356 (5 pages in English).

* cited by examiner

*Primary Examiner* — Alicia L Otton
(74) *Attorney, Agent, or Firm* — NSIP Law

(57) ABSTRACT

The present invention relates to a 6-phenoxypyrimidine derivative, a method for preparing the compound and a pharmaceutical composition containing the compound as an active ingredient. Because the 6-phenoxypyrimidine compound represented by Chemical Formula 1 according to the present invention has an activity of inhibiting the production of nitric oxide (NO) as an inflammation-related factor, it is useful in treating and preventing inflammatory diseases including immunological diseases.

16 Claims, 9 Drawing Sheets

[FIG 1]
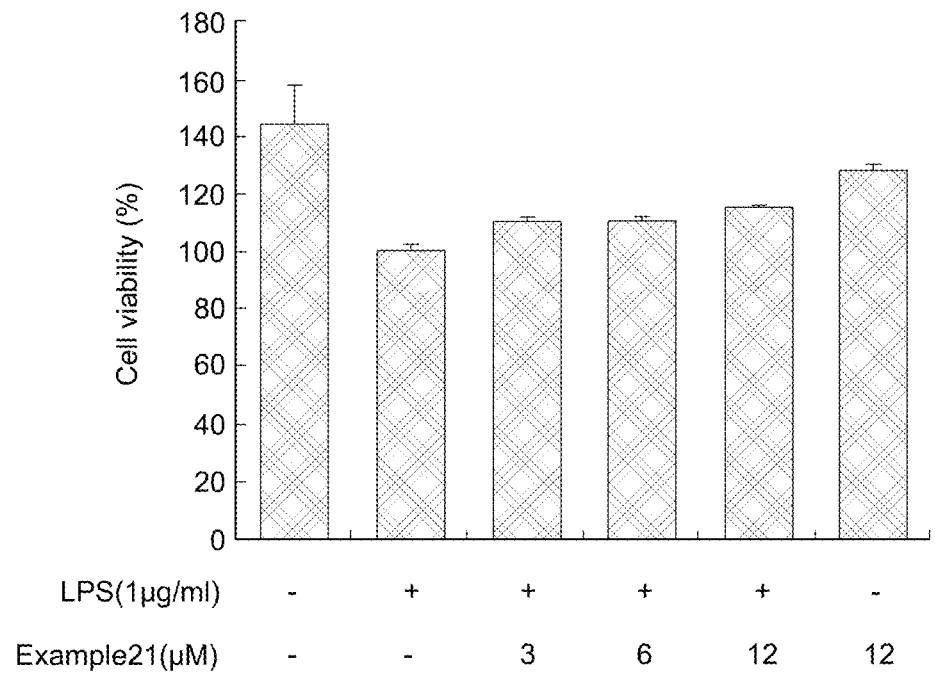
[FIG 2]
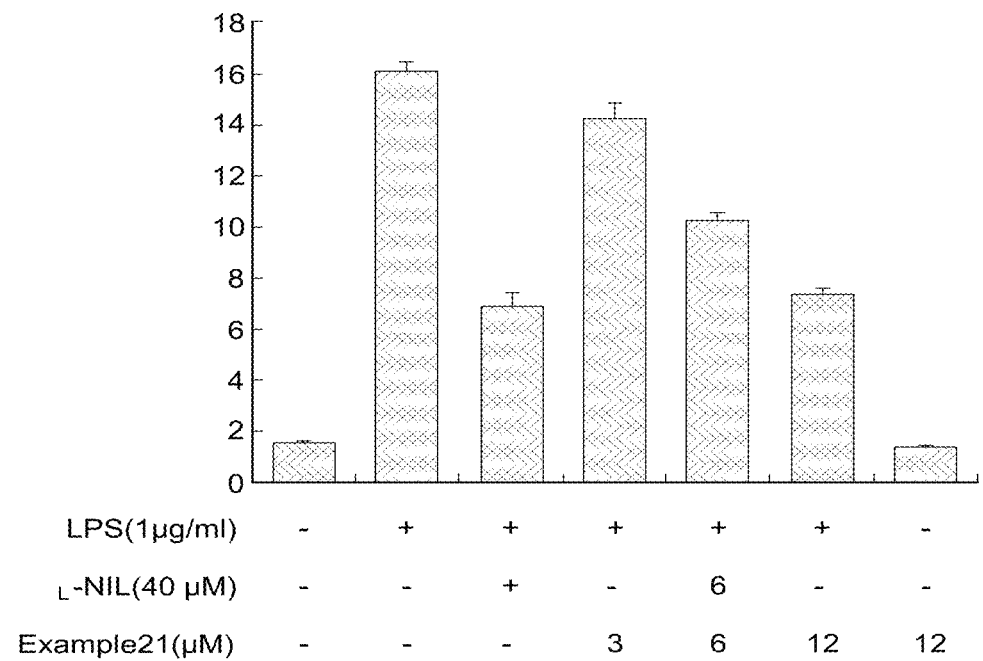

[FIG 3]
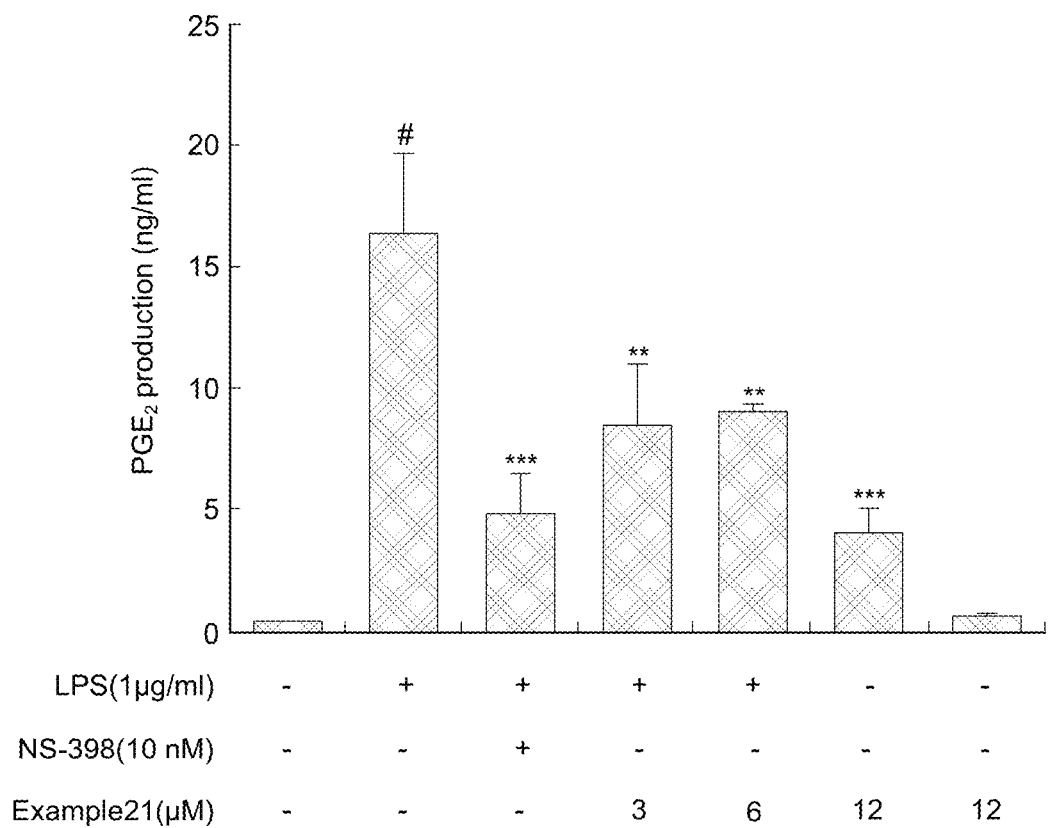

[FIG 4]
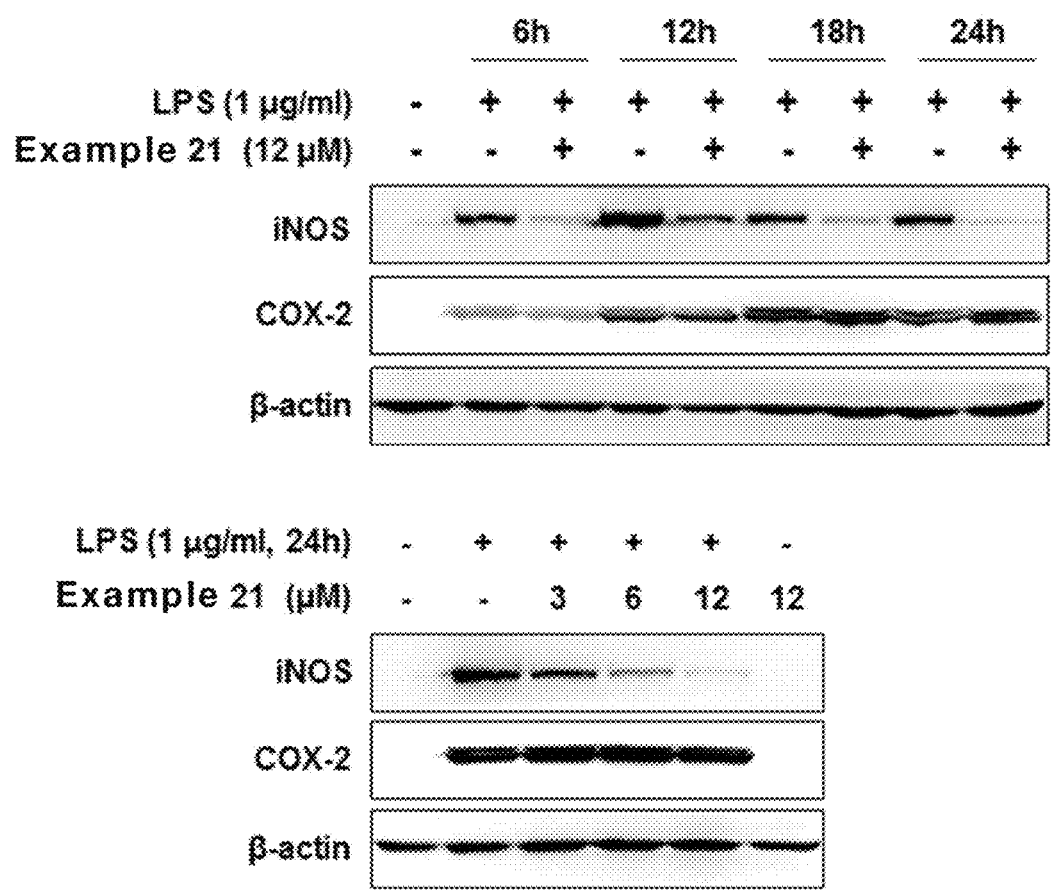

[FIG 5A]
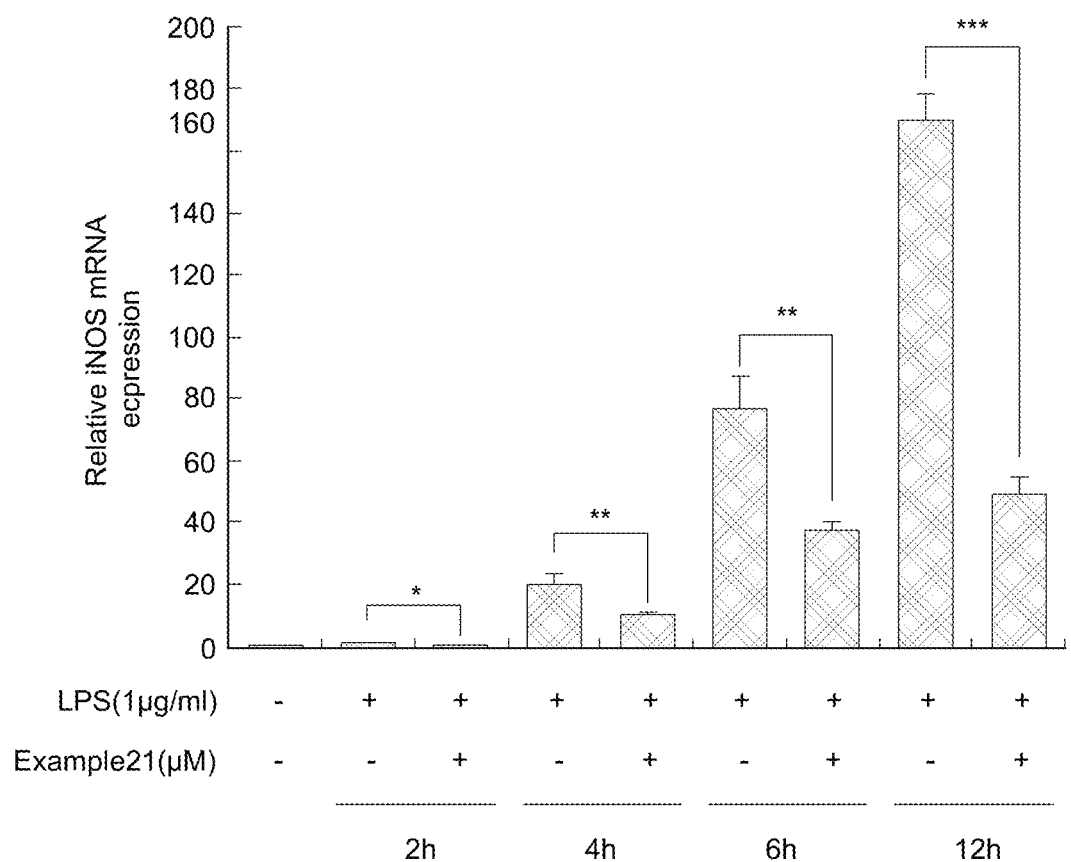

[FIG 5B]
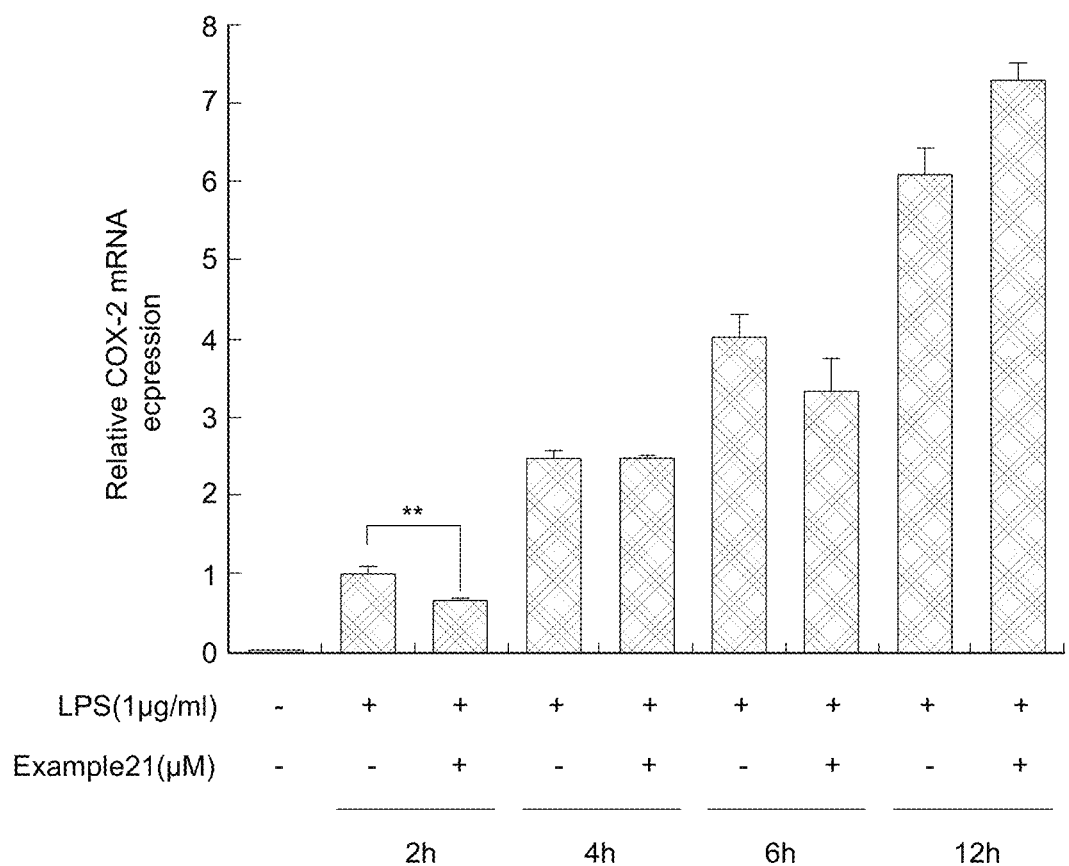

[FIG 6A]
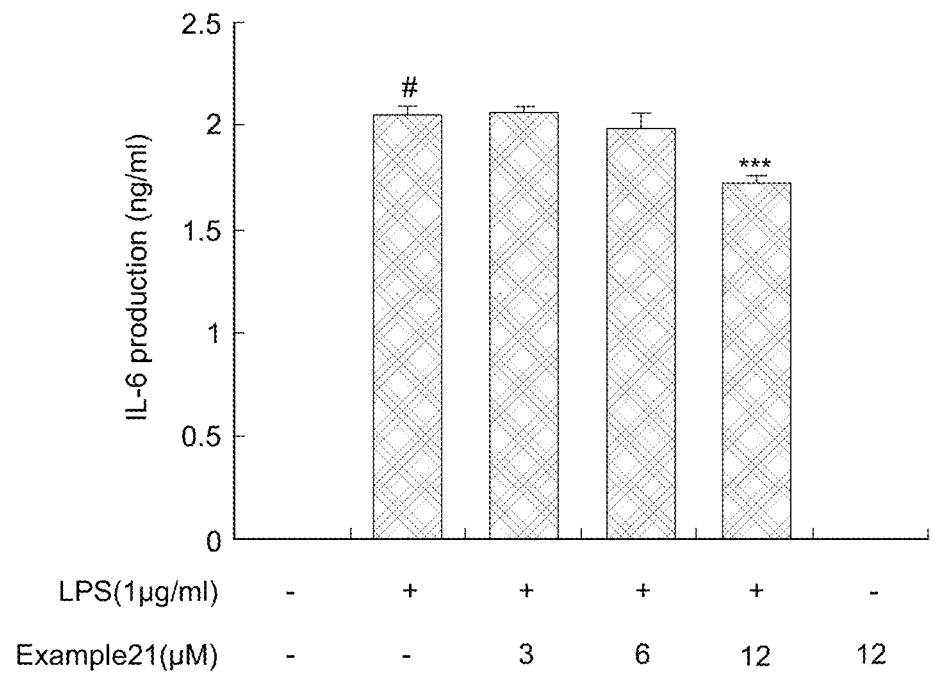
[FIG 6B]
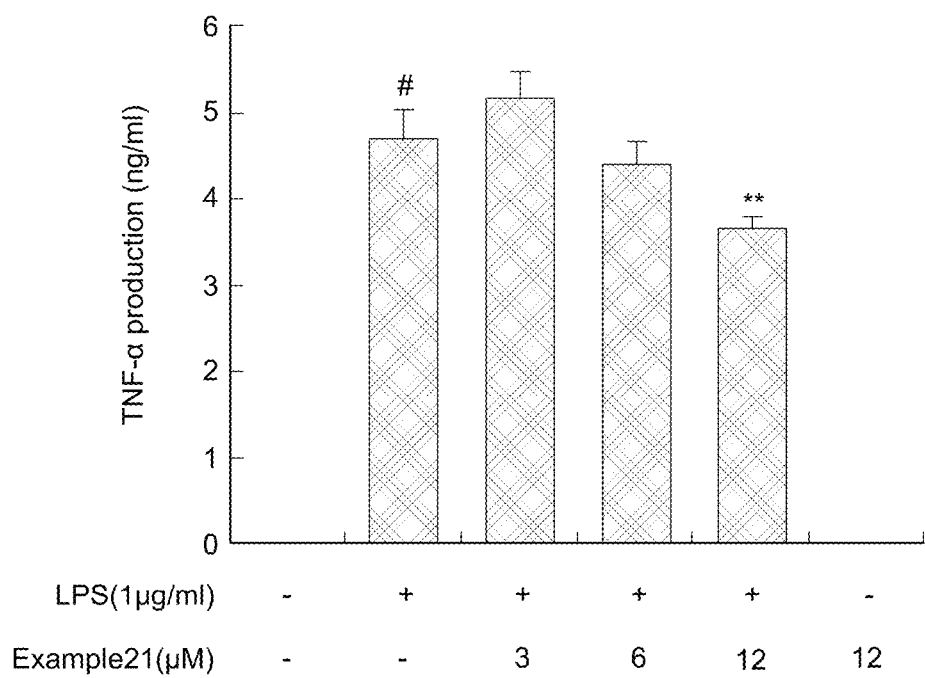

[FIG 6C]
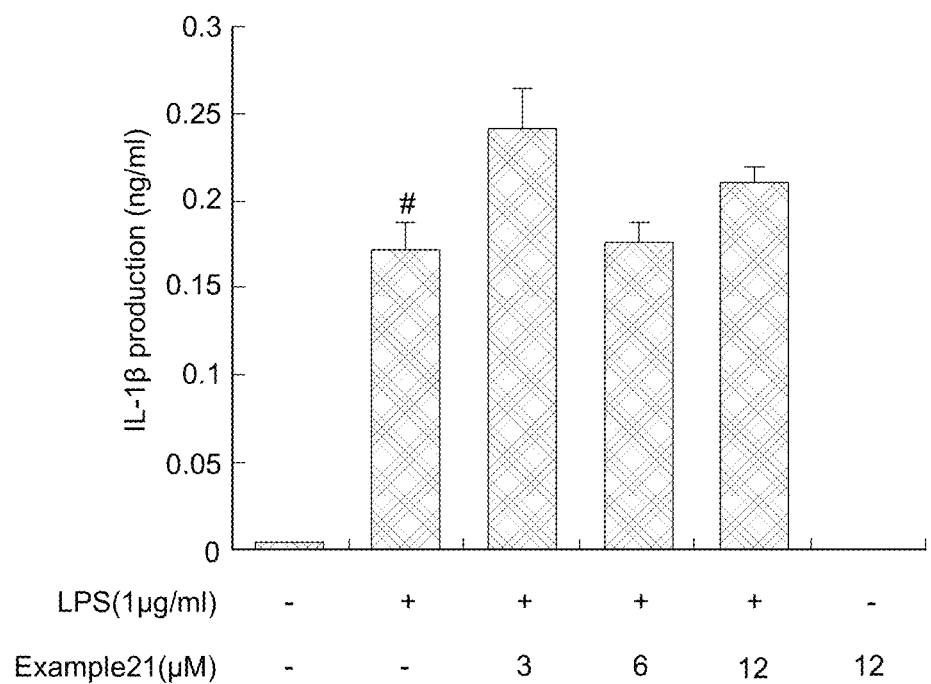

[FIG 7A]
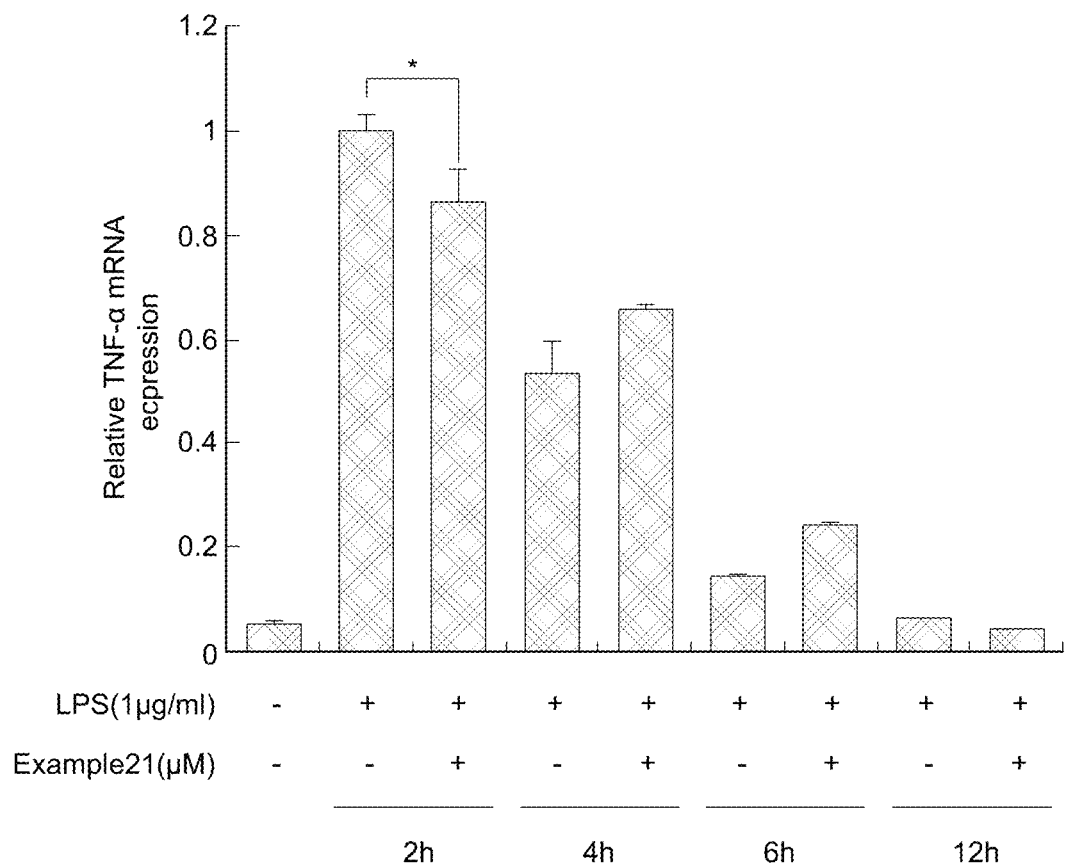

[FIG 7B]
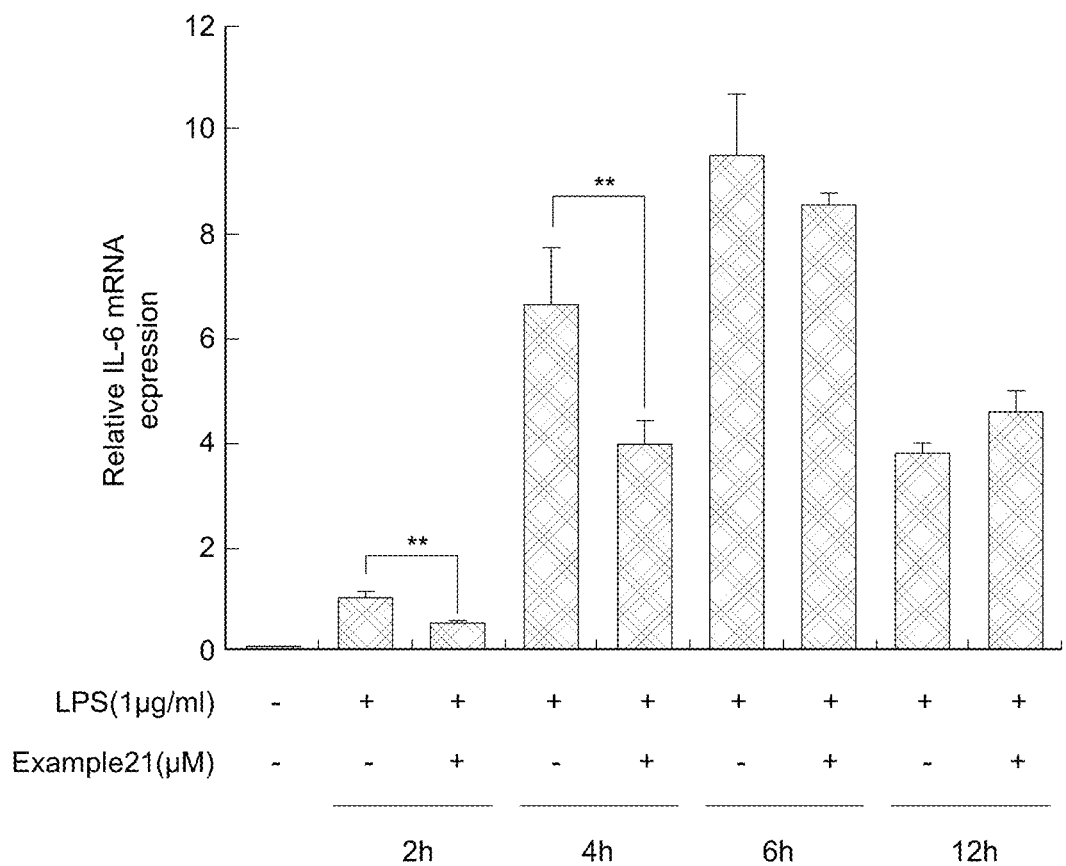

ANTI-INFLAMMATORY 6-PHENOXYPYRIMIDINE DERIVATIVES, PROCESS FOR THEIR PREPARATION AND PHARMACEUTICAL COMPOSITION CONTAINING THEM

CROSS-REFERENCE TO RELATED APPLICATIONS

This application claims, under 35 U.S.C. § 119, the priority of Korean Patent Application No. 10-2017-0079664, filed on Jun. 23, 2017, in the Korean Intellectual Property Office, the disclosure of which is incorporated herein by reference in its entirety.

BACKGROUND

(a) Technical Field

The present invention relates to a 6-phenoxypyrimidine derivative having anti-inflammatory activity, a method for preparing the compound and a pharmaceutical composition containing the compound as an active ingredient.

(b) Background Art

It is known that inflammatory response is caused by very complicated biochemical reactions. There are various mediators that induce inflammatory diseases such as prostaglandins, leukotrienes, platelet-activating factor, nitric oxide (NO), proinflammatory cytokines, etc. Therefore, substances that can inhibit the production of or decrease the activity of various mediators related with inflammatory responses are searched to discover anti-inflammatory substances. In general, in order to elucidate the usefulness as a medication for treatment of inflammations, endotoxins of Gram-negative bacteria such as lipopolysaccharides (LPS) are activated for the murine macrophage cell line RAW 264.7 and then the inhibition of the production of inflammatory mediators is investigated after treating with the test substance.

Nitric oxide (NO) is known as an important mediator molecule involved in inflammatory responses. Many reactive substances such as NO, etc. synthesized by nitric oxide (NO) synthase (NO synthase), particularly inducible nitric oxide synthase (iNOS), are involved in pathological conditions related with inflammations. That is to say, it is reported that iNOS is overexpressed due to the stimulation by LPS and induces inflammatory diseases including immunological diseases (see non-patent documents 1 and 2). In addition, it is known that the overexpression of iNOS caused by other stimulations such as proinflammatory cytokines, etc. induces some inflammatory and autoimmune diseases.

REFERENCES OF THE RELATED ART

Patent Documents (Patent document 1) International Patent Publication No. WO 2005/037800.
(Patent document 2) International Patent Publication No. WO 2009/145856.

Non-Patent Documents (Non-patent document 1) "Nitric Oxide in Arthritis", *Free Radical Biology and Medicine*, 1998, Vol. 24, pp. 1511-1519.

(Non-patent document 2) "Nitric oxide and inflammatory arthritides", *Life Science*, 1997, Vol. 61, pp. 2073-2081.

SUMMARY

The present invention is directed to providing a 6-phenoxypyrimidine derivative having a novel chemical structure or a pharmaceutically acceptable salt thereof.

The present invention is also directed to providing a method for preparing the novel compound.

The present invention is also directed to providing a pharmaceutical composition containing the novel compound as an active ingredient.

The present invention provides a 6-phenoxypyrimidine derivative represented by Chemical Formula 1 or a pharmaceutically acceptable salt thereof:

[Chemical Formula 1]

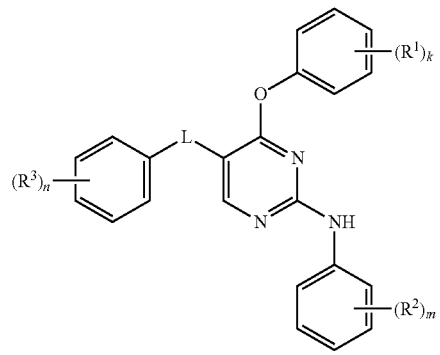

wherein
L is —C(O)NH—, —NHC(O)NH—, —CH=N— or —CH$_2$—NH—;

$R^1$ is a halogen atom, a $C_1$-$C_{10}$ alkyl group, a $C_1$-$C_{10}$ alkoxy group or a $C_1$-$C_{10}$ haloalkyl group substituted with 1-10 halogen atom(s);

$R^2$ is a 5- or 6-membered heterocycle group substituted with 1-3 heteroatom(s) selected from a group consisting of N and O or a $C_1$-$C_{10}$ alkoxy group;

$R^3$ is a halogen atom, a $C_1$-$C_{10}$ alkyl group, a $C_1$-$C_{10}$ alkoxy group or a $C_1$-$C_{10}$ haloalkyl or $C_1$-$C_{10}$ haloalkoxy group substituted with 1-13 halogen atom(s); and k, m and n are integers from 0 to 3 as the number of substituents.

The present invention also provides a method for preparing the 6-phenoxypyrimidine derivative represented by Chemical Formula 1.

In addition, the present invention provides a pharmaceutical composition containing the phenoxypyrimidine derivative represented by Chemical Formula 1 as an active ingredient.

Because the 6-phenoxypyrimidine compound represented by Chemical Formula 1 according to the present invention has an activity of inhibiting the production of nitric oxide (NO) as an inflammation-related factor, it is useful in treating and preventing inflammatory diseases including immunological diseases.

The inflammatory diseases that may be treated or prevented by the 6-phenoxypyrimidine compound represented by Chemical Formula 1 may include rheumatoid arthritis, psoriatic arthritis, inflammatory bowel disease, Crohn's disease, etc.

BRIEF DESCRIPTION OF DRAWINGS

FIG. 1 shows the cell viability for (E)-5-((3,5-dimethoxybenzylidene)amino)-4-(4-methoxyphenoxy)-N-(4-morpholinophenyl)pyrimidin-2-amine (Example 21).

FIG. 2 shows the NO inhibitory effect of (E)-5-((3,5-dimethoxybenzylidene)amino)-4-(4-methoxyphenoxy)-N-(4-morpholinophenyl)pyrimidin-2-amine (Example 21).

FIG. 3 shows the PEG2 production inhibiting activity by (E)-5-((3,5-dimethoxybenzylidene)amino)-4-(4-methoxyphenoxy)-N-(4-morpholinophenyl)pyrimidin-2-amine (Example 21).

FIG. 4 shows the western blotting result of (E)-5-((3,5-dimethoxybenzylidene)amino)-4-(4-methoxyphenoxy)-N-(4-morpholinophenyl)pyrimidin-2-amine (Example 21).

FIGS. 5A and 5B show the iNOS mRNA expression level and COX-2 mRNA expression level for (E)-5-((3,5-dimethoxybenzylidene)amino)-4-(4-methoxyphenoxy)-N-(4-morpholinophenyl)pyrimidin-2-amine (Example 21).

FIGS. 6A, 6B and 6C show the IL-6, TNF-α and IL-1β production inhibiting activity by (E)-5-((3,5-dimethoxybenzylidene)amino)-4-(4-methoxyphenoxy)-N-(4-morpholinophenyl)pyrimidin-2-amine (Example 21).

FIGS. 7A and 7B show the TNF-α mRNA expression level and IL-6 mRNA expression level for (E)-5-((3,5-dimethoxybenzylidene)amino)-4-(4-methoxyphenoxy)-N-(4-morpholinophenyl)pyrimidin-2-amine (Example 21).

DETAILED DESCRIPTION

The present invention provides a 6-phenoxypyrimidine derivative represented by Chemical Formula 1 or a pharmaceutically acceptable salt thereof:

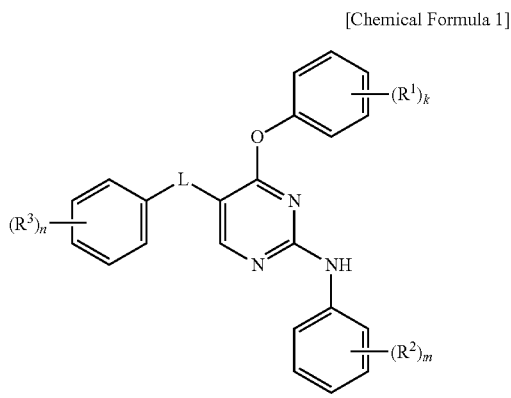

[Chemical Formula 1]

wherein

L is —C(O)NH—, —NHC(O)NH—, —CH=N— or —CH$_2$—NH—;

$R^1$ is a halogen atom, a $C_1$-$C_{10}$ alkyl group, a $C_1$-$C_{10}$ alkoxy group or a $C_1$-$C_{10}$ haloalkyl group substituted with 1-10 halogen atom(s);

$R^2$ is a 5- or 6-membered heterocycle group substituted with 1-3 heteroatom(s) selected from a group consisting of N and O or a $C_1$-$C_{10}$ alkoxy group;

$R^3$ is a halogen atom, a $C_1$-$C_{10}$ alkyl group, a $C_1$-$C_{10}$ alkoxy group or a $C_1$-$C_{10}$ haloalkyl or $C_1$-$C_{10}$ haloalkoxy group substituted with 1-13 halogen atom(s); and k, m and n are integers from 0 to 3 as the number of substituents.

The compound according to the present invention includes a pharmaceutically acceptable salt of the compound represented by Chemical Formula 1. The pharmaceutically acceptable salt should have low toxicity in the human body and should not negatively affect the biological activity and physicochemical properties of the parent compound. The pharmaceutically acceptable salt may be an acid addition salt of a pharmaceutically acceptable free acid and the base compound of Chemical Formula 1, an alkali metal salt (sodium salt, etc.), an alkaline earth metal salt (calcium salt, etc.), an organic base addition salt of an organic base and a carboxylic acid of Chemical Formula 1 or an amino acid addition base. The free acid that may be used to prepare the pharmaceutically acceptable salt may be an inorganic acid or an organic acid. The inorganic acid may be hydrochloric acid, sulfuric acid, nitric acid, phosphoric acid, perchloric acid, bromic acid, etc. The organic acid may be acetic acid, methanesulfonic acid, ethanesulfonic acid, p-toluenesulfonic acid, trifluoroacetic acid, fumaric acid, maleic acid, malonic acid, phthalic acid, succinic acid, lactic acid, citric acid, gluconic acid, tartaric acid, salicylic acid, malic acid, oxalic acid, benzoic acid, embonic acid, aspartic acid, glutamic acid, etc. The organic base that may be used to prepare the organic base addition salt may be tris(hydroxymethyl) methylamine, dicyclohexylamine, etc. An amino acid that may be used to prepare the amino acid addition base may be a natural amino acid such as alanine, glycine, etc.

The compound according to the present invention also includes a hydrate or solvate of the compound represented by Chemical Formula 1. The hydrate or solvate may be prepared by a common method. For example, it may be prepared by dissolving the base compound of Chemical Formula 1 in a solvent such as water, methanol, ethanol, acetone or 1,4-dioxane and then crystallizing or recrystallizing the same after adding a free acid or a free base.

Also, the compound represented by Chemical Formula 1 may have one or more asymmetric center and, in this case, the compound may exist as an enantiomer or diastereomer. In addition, if the L in the compound represented by Chemical Formula 1 is —CH=N—, the compound may exist as a cis or trans isomer. Accordingly, the compound of the present invention includes the isomers or a mixture of the isomers. The different isomers may be separated or resolved by a common method and specific isomers may be obtained by stereospecific or asymmetric synthesis according to a common synthesis method.

The compound of the present invention also includes a radioactive derivative of the compound represented by Chemical Formula 1. The radioactive compound is useful in biological researches.

Hereinafter, the substituents used to define the compound represented by Chemical Formula 1 are described in more detail.

In the present invention, the term 'halo' or 'halogen atom', which can be used interchangeably, means chloro, fluoro, bromo or iodo.

In the present invention, the 'alkyl group' refers to a straight, branched or cyclic aliphatic saturated hydrocarbon group having 1-10 carbon atom(s), specifically 1-6 carbon atom(s), more specifically 1-4 carbon atom(s). Specific examples of the alkyl group may include a methyl group, an ethyl group, a n-propyl group, an isopropyl group, a cyclopropyl group, a cyclopropylmethyl group, a n-butyl group, an isobutyl group, a tert-butyl group, a cyclobutyl group, a n-pentyl group, an isopentyl group, a neopentyl group, tert-pentyl group, cyclopentyl group, a n-hexyl group, isohexyl group, cyclohexyl group, a n-heptyl group, an n-octyl group, etc.

In the present invention, the 'haloalkyl group' refers to a straight or branched carbon chain containing 1-13 halogen atom(s) such as fluoro, chloro, bromo or iodo and having 1-10 carbon atom(s). Specific examples of the haloalkyl group may include a fluoromethyl group, a trifluoromethyl group, a 1,2-dichloroethyl group, a 1,1-dichloroethyl group, a pentafluoroethyl group, etc.

Specifically, in the compound represented by Chemical Formula 1 according to the present invention, the L is —C(O)NH—, —NHC(O)NH—, —CH=N— or —CH$_2$—NH—; the R$^1$ is a halogen atom, a C$_1$-C$_6$ alkyl group, a C$_1$-C$_6$ alkoxy group or a C$_1$-C$_{10}$ haloalkyl group substituted with 1-10 halogen atom(s); the R$^2$ is a morpholine group or a C$_1$-C$_6$ alkoxy group; the R$^3$ is a halogen atom, a C$_1$-C$_6$ alkoxy group or a C$_1$-C$_6$ haloalkyl or C$_1$-C$_6$ haloalkoxy group substituted with 1-10 halogen atom(s); and the k, m and n are integers 1 or 2 as the number of substituents.

Specifically, the compound represented by Chemical Formula 1 according to the present invention may be a compound represented by Chemical Formula 1a wherein the L is —C(O)NH—:

[Chemical Formula 1a]

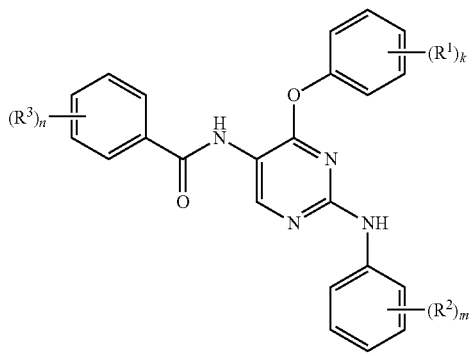

wherein
R$^1$ is a C$_1$-C$_6$ alkyl group or a C$_1$-C$_6$ alkoxy group;
R$^2$ is a morpholine group or a C$_1$-C$_6$ alkoxy group;
R$^3$ is a C$_1$-C$_6$ alkoxy group; and
k, m and n are integers 1 or 2 as the number of substituents.

Specifically, the compound represented by Chemical Formula 1 according to the present invention may be a compound represented by Chemical Formula 1b wherein the L is —NHC(O)NH—:

[Chemical Formula 1b]

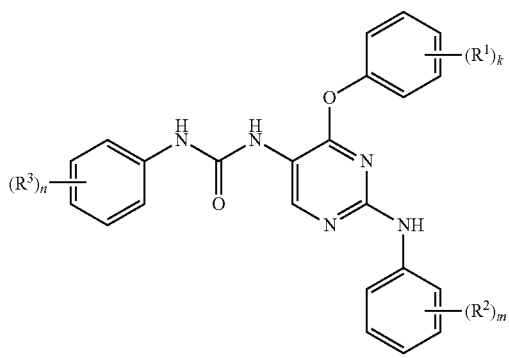

wherein
R$^1$ is a halogen atom, a C$_1$-C$_6$ alkyl group, a C$_1$-C$_6$ alkoxy group or a C$_1$-C$_6$ haloalkyl group substituted with 1-10 halogen atom(s);
R$^2$ is a morpholine group or a C$_1$-C$_6$ alkoxy group;
R$^3$ is a halogen atom, a C$_1$-C$_6$ alkoxy group or a C$_1$-C$_6$ haloalkyl group substituted with 1-10 halogen atom(s); and
k, m and n are integers 1 or 2 as the number of substituents.

Specifically, the compound represented by Chemical Formula 1 according to the present invention may be a compound represented by Chemical Formula 1c wherein the L is —CH=N—:

[Chemical Formula 1c]

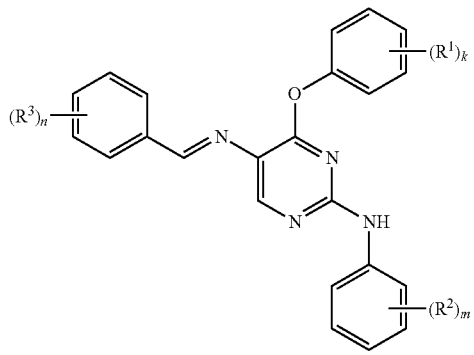

wherein
R$^1$ is a C$_1$-C$_6$ alkyl group or a C$_1$-C$_6$ alkoxy group;
R$^2$ is a morpholine group;
R$^3$ is a halogen atom, C$_1$-C$_6$ alkoxy group or a C$_1$-C$_6$ haloalkyl or C$_1$-C$_6$ haloalkoxy group substituted with 1-10 halogen atom(s); and
k, m and n are integers 1 or 2 as the number of substituents.

Specifically, the compound represented by Chemical Formula 1 according to the present invention may be a compound represented by Chemical Formula 1d wherein the L is —CH$_2$—NH—:

[Chemical Formula 1d]

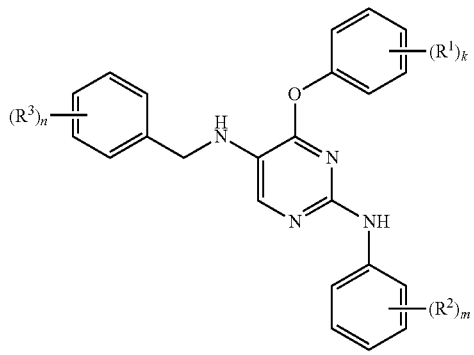

wherein
R$^1$ is a C$_1$-C$_6$ alkyl group or a C$_1$-C$_6$ alkoxy group;
R$^2$ is a morpholine group;
R$^3$ is a halogen atom, a C$_1$-C$_6$ alkoxy group or a C$_1$-C$_6$ haloalkyl or C$_1$-C$_6$ haloalkoxy group substituted with 1-10 halogen atom(s); and k, m and n are integers 1 or 2 as the number of substituents.

Specific examples of the compound represented by Chemical Formula 1 are as follows:
1) N-(2-(3,5-dimethoxyphenylamino)-4-(2-methoxy-4-methylphenoxy)methylphenoxy)-3,5-dimethoxybenzamide;
2) 3,5-dimethoxy-N-(4-(2-methoxy-4-methylphenoxy)-2-(4-morpholinophenylamino)methylphenoxy)benzamide;
3) 1-(3,5-dimethoxyphenyl)-3-(2-(3,5-dimethoxyphenylamino)-4-(2-methoxy-4-methylphenoxy)methylphenoxy)urea;
4) 1-(3,5-dimethoxyphenyl)-3-(4-(2-methoxy-4-methylphenoxy)-2-(4-morpholinophenylamino)methylphenoxy)urea;
5) 1-(2-(3,5-dimethoxyphenylamino)-4-(2-methoxy-4-methylphenoxy)methylphenoxy)-3-(4-methoxyphenyl)urea;
6) 1-(2,6-dichlorophenyl)-3-(2-(3,5-dimethoxyphenylamino)-4-(2-methoxy-4-methylphenoxy)methylphenoxy)urea;
7) 1-(2,6-dichlorophenyl)-3-(4-(2-methoxy-4-methylphenoxy)-2-(4-morpholinophenylamino)methylphenoxy)urea;
8) 1-(3,5-dichlorophenyl)-3-(4-(2-methoxy-4-methylphenoxy)-2-((4-morpholinophenyl)amino)methylphenoxy)urea;
9) 1-(4-(2-methoxy-4-methylphenoxy)-2-((4-morpholinophenyl)amino)methylphenoxy)-3-(2-methoxyphenyl)urea;
10) 1-(3,5-dimethoxyphenyl)-3-(4-(3-methoxyphenoxy)-2-((4-morpholinophenyl)amino) methylphenoxy)urea;
11) 1-(3,5-dimethoxyphenyl)-3-(2-(4-morpholinophenylamino)-4-(4-(trifluoromethyl)phenoxy)methylphenoxy)urea;
12) 1-(3,5-dimethoxyphenyl)-3-(4-(4-fluorophenoxy)-2-(4-morpholinophenylamido)methylphenoxy)urea;
13) 1-(3,5-bistrifluoromethylphenyl)-3-(4-(2-methoxy-4-methylphenoxy)-2-((2-morpholinophenyl)amino)methylphenoxy)urea;
14) 1-(3,5-dichlorophenyl)-3-(4-(3-methoxyphenoxy)-2-((2-morpholinophenyl)amino)methylphenoxy)urea;
15) 1-(2,6-dichlorophenyl)-3-(4-(3-methoxyphenoxy)-2-((2-morpholinophenyl)amino)methylphenoxy)urea;
16) (E)-5-((3,5-dimethoxybenzylidene)amino)-4-(2-methoxy-4-methylphenoxy)-N-(4-morpholinophenyl)pyrimidin-2-amine;
17) (E)-5-((3,5-dimethoxybenzylidene)amino)-4-(3-methoxyphenoxy)-N-(4-morpholinophenyl)pyrimidin-2-amine;
18) (E)-5-((2-chlorobenzylidene)amino)-4-(2-methoxy-4-methylphenoxy)-N-(4-morpholinophenyl)pyrimidin-2-amine;
19) (E)-5-((3-chlorobenzylidene)amino)-4-(2-methoxy-4-methylphenoxy)-N-(4-morpholinophenyl)pyrimidin-2-amine;
20) (E)-4-(4-(trifluoromethyl)phenoxy)-N-(4-morpholinophenyl)-5-((3,5-dimethoxybenzylidene)amino)pyrimidin-2-amine;
21) (E)-5-((3,5-dimethoxybenzylidene)amino)-4-(4-methoxyphenoxy)-N-(4-morpholinophenyl)pyrimidin-2-amine;
22) (E)-5-((4-chlorobenzylidene)amino)-4-(2-methoxy-4-methylphenoxy)-N-(4-morpholinophenyl)pyrimidin-2-amine;
23) (E)-5-((3,5-dimethoxybenzylidene)amino)-4-(4-fluorophenoxy)-N-(4-morpholinophenyl)pyrimidin-2-amine;
24) (E)-4-(2-methoxy-4-methylphenoxy)-N-(4-morpholinophenyl)-5-((3,5-dichlorobenzylidene)amino)pyrimidin-2-amine;
25) (E)-4-(2-methoxy-4-methylphenoxy)-N-(4-morpholinophenyl)-5-((3-(trifluoromethoxy)benzylidene)amino)pyrimidin-2-amine;
26) (E)-5-((3-isopropoxybenzylidene)amino)-4-(2-methoxy-4-methylphenoxy)-N-(4-morpholinophenyl)pyrimidin-2-amine;
27) (E)-5-((3,5-bis(trifluoromethyl)benzylidene)amino-4-(2-methoxy-4-methylphenoxy)-N-(4-morpholinophenyl)pyrimidin-2-amine;
28) (E)-5-((3,5-dichlorobenzylidene)amino)-4-(4-methoxyphenoxy)-N-(4-morpholinophenyl)pyrimidin-2-amine;
29) N5-(3,5-bis(trifluoromethyl)benzyl)-4-(2-methoxy-4-methylphenoxy)-N2-(4-morpholinophenyl)pyrimidine-2,5-diamine;
30) 4-(2-methoxy-4-methylphenoxy)-N2-(4-morpholinophenyl)-N5-(3-(trifluoro)benzyl)pyrimidine-2,5-diamine;
31) 4-(2-methoxy-4-methylphenoxy)-N2-(morpholinophenyl)-N4-(4-(trifluoromethoxy)benzyl)pyrimidine-2,5-diamine;
32) N4-(4-chlorobenzyl)-4-(2-methoxy-4-methylphenoxy)-N2-(4-morpholinophenyl)pyrimidine-2,5-diamine;
33) N5-(3,5-dimethoxybenzyl)-4-(2-methoxy-4-methylphenoxy)-N2-(4-morpholinophenyl)pyrimidine-2,5-diamine; and
a pharmaceutically acceptable salt thereof.

The present invention also provides a pharmaceutical composition containing a compound selected from a group consisting of the 6-phenoxypyrimidine derivative represented by Chemical Formula 1 and a pharmaceutically acceptable salt thereof as an active ingredient.

The present invention provides an agent for preventing or treating an inflammatory disease, which contains a compound selected from a group consisting of the 6-phenoxypyrimidine derivative represented by Chemical Formula 1 and a pharmaceutically acceptable salt thereof as an active ingredient. In the present invention, the inflammatory disease is a disease caused by the increased production of nitric oxide (NO) as an inflammation-related factor and may include, specifically, rheumatoid arthritis, psoriatic arthritis, inflammatory bowel disease, Crohn's disease, etc.

The pharmaceutical composition may be applied to a laboratory animal such as mouse, rabbit, rat, guinea pig or hamster, a primate including human, etc., although not being limited thereto. Specifically, it may be applied to a primate including human, more specifically human.

In the present invention, 'prevention' refers to any action taken to inhibit an inflammatory disease or delay its onset by administering the pharmaceutical composition according to the present invention.

In the present invention, 'treatment' may be interpreted to include alleviation or improvement of symptoms, reduction of the scope of a disease, delay or alleviation of the progress of a disease, improvement, alleviation or stabilization of a disease condition, partial or complete recovery, extension of survival and other therapeutically favorable results.

The content of the active ingredient, i.e., the compound represented by Chemical Formula 1, a pharmaceutically acceptable salt or a hydrate thereof, may be controlled adequately by those skilled in the art depending on the mode and method of using the pharmaceutical composition of the present invention.

The pharmaceutical composition of the present invention contains a compound selected from a group consisting of the 6-phenoxypyrimidine derivative represented by Chemical Formula 1 and a pharmaceutically acceptable salt thereof as an active ingredient and the active ingredient may be contained in an amount of 0.1-10 wt %, more specifically 0.5-5 wt %, based on the total weight of the pharmaceutical composition.

The pharmaceutical composition of the present invention may contain only the compound selected from a group consisting of the 6-phenoxypyrimidine derivative represented by Chemical Formula 1 and a pharmaceutically acceptable salt thereof as an active ingredient and may also contain a pharmaceutically acceptable carrier, excipient, diluent or adjuvant.

For example, the pharmaceutically acceptable carrier, excipient or diluent may be one or more selected from a group consisting of lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, dextrin, calcium carbonate, propylene glycol, liquid paraffin and physiological saline. However, any commonly used carrier, excipient or diluent may be used without being limited thereto. Also, the pharmaceutical composition may further contain a commonly used filler, extender, binder, disintegrant, antiadherent, lubricant, wetting agent, pH control agent, nutrient, vitamin, electrolyte, alginic acid and its salt, pectic acid and its salt, protective colloid, glycerin, fragrance, emulsifier, antiseptic, etc.

The compound selected from the 6-phenoxypyrimidine derivative represented by Chemical Formula 1 and a pharmaceutically acceptable salt thereof according to the present invention may be administered together with another anti-inflammatory agent for treating an inflammatory disease in order to enhance the therapeutic effect of the anti-inflammatory agent.

Specifically, the pharmaceutical composition may further contain, in addition to the active ingredient, one or more another anti-inflammatory agent or therapeutic agent known to be effective in treating or preventing inflammations, which may be administered simultaneously or at different times.

The pharmaceutical composition may be administered either orally or parenterally. It may be administered through various routes including, for example, oral, transdermal, subcutaneous, intravenous or intramuscular routes. Also, the formulation type of the composition may vary depending on how it is used. It may be formulated by a method well known in the art to which the present invention belongs, so that the active ingredient can be released immediately, in a sustained manner or in a controlled manner after being administered to a mammal. In general, solid formulations for oral administration include a tablet, a pill, a soft or hard capsule, a powder, a granule, etc. and may be prepared by mixing with one or more excipient, e.g., starch, calcium carbonate, sucrose, lactose, gelatin, etc. In addition to the simple excipient, a lubricant such as magnesium stearate and talc may also be used. Liquid formulations for oral administration may include a suspension, an internal solution, an emulsion, a syrup, etc. and may contain, in addition to a commonly used simple diluent such as water and liquid paraffin, various excipients, e.g., a wetting agent, a sweetener, an aromatic, a preservative, etc. Formulations for parenteral may include a cream, a lotion, an ointment, a plaster, a liquid, a solution, an aerosol, a fluid extract, an elixir, an infusion, a sachet, a patch, an injection, etc. Specifically, a formulation for injection may be in the form of an isotonic aqueous solution or a suspension.

The pharmaceutical composition may further contain an adjuvant such as a sterilant, an antiseptic, a stabilizer, a hydrating agent, an emulsification accelerant, a salt and/or buffer for control of osmotic pressure, etc. and other therapeutically useful materials and may be formulated by a common mixing, granulation or coating method or other adequate methods known in the art.

The administration dosage of the pharmaceutical composition may be determined in consideration of the administration method, the age and sex of a subject, the severity and condition of a disease, the absorptivity of the active ingredient in the body, deactivation ratio and the drug administered together and the administration may be made at once or in divided doses. Specifically, the administration dosage of the active ingredient of the pharmaceutical composition may be 0.001-100 mg/kg body weight, specifically 0.01-35 mg/kg body weight, per day for a mammal including human and the administration may be made through oral or parenteral routes once or several times a day.

The present invention also provides a method for treating an inflammatory disease, which includes a step of administering a therapeutically effective amount of a compound selected from a group consisting of the 6-phenoxypyrimidine derivative represented by Chemical Formula 1 and a pharmaceutically acceptable salt thereof.

Specifically, the method may further include a step of identifying a patient in need of the prevention or treatment of the inflammatory disease before the administration step.

In the present invention, the "therapeutically effective amount" refers to an amount of the active ingredient which is effective for prevention or treatment of an inflammatory disease of a mammal. The therapeutically effective amount may be controlled depending on various factors including the kind of the disease, the severity of the disease, the kind and content of the active ingredient and other ingredients contained in the composition, the type of formulation, the age, body weight, general health condition, sex and diet of the patient, administration time, administration route, the clearance ratio of the composition, treatment period and the drug used together. Specifically, the therapeutically effective amount may be 0.001-100 mg/kg-body weight, specifically 0.01-35 mg/kg-body weight, per day and the administration may be made through oral or parenteral routes once or several times a day.

The present invention also provides a method for preparing the 6-phenoxypyrimidine derivative represented by Chemical Formula 1.

The preparation method according to the present invention may be divided into four preparation methods depending on whether the L is —C(O)NH—, —NHC(O)NH—, —CH=N— or —CH$_2$—NH—.

As a first preparation method, a method for preparing a 6-phenoxypyrimidine derivative wherein the L is —C(O)NH includes:

(step a) a step of preparing a compound represented by Chemical Formula 4 by reacting 2,4-dichloro-5-nitropyrimidine represented by Chemical Formula 2 with a phenol compound represented by Chemical Formula 3;

(step b) a step of preparing a compound represented by Chemical Formula 6 by reacting the compound represented by Chemical Formula 4 with an aniline derivative represented by Chemical Formula 5;

(step c) a step of preparing an amine compound represented by Chemical Formula 7 by reducing the nitro compound represented by Chemical Formula 6; and (step d-1) a step of preparing a compound represented by Chemical Formula 1a by reacting the amine compound represented by Chemical Formula 7 with an acid chloride derivative represented by Chemical Formula 8-1.

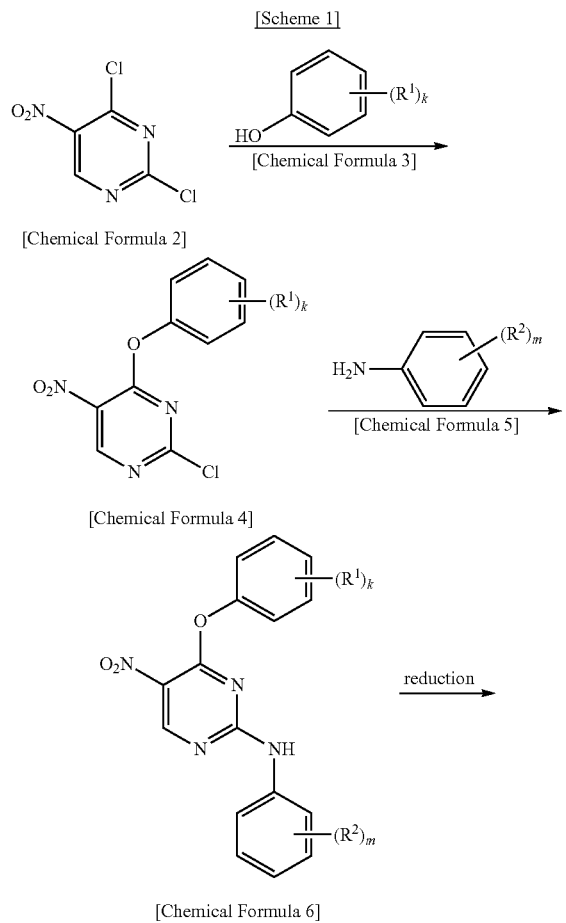

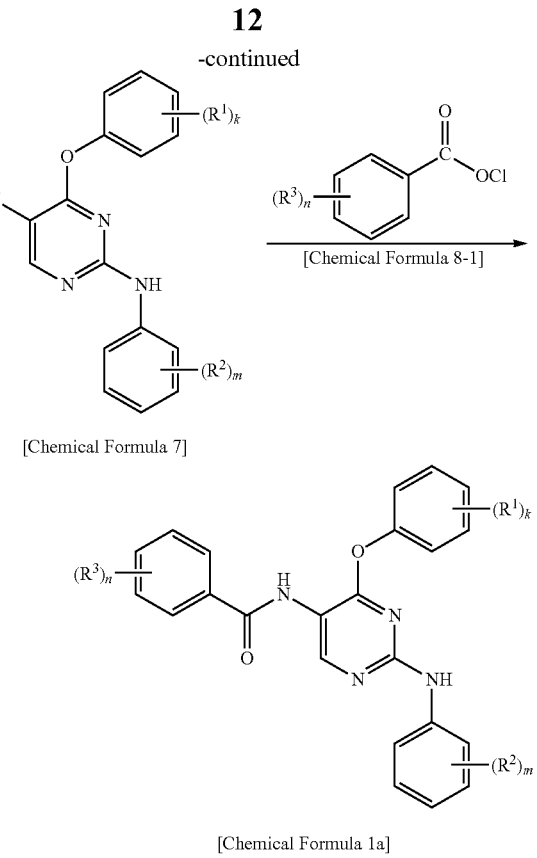

In Scheme 1, $R^1$, $R^2$, $R^3$, k, m and n are the same as defined above in Chemical Formula 1.

The steps of the first preparation method of the present invention illustrated in Scheme 1 are described in more detail.

Step a

In the (step a), the compound represented by Chemical Formula 4 is prepared by reacting the 2,4-dichloro-5-nitropyrimidine represented by Chemical Formula 2 used as a starting material with the phenol compound represented by Chemical Formula 3.

The compound represented by Chemical Formula 2 used as the starting material is commercially available and may also be prepared by a common organic synthesis method. The reaction of the (step a) is well known in the field of organic chemistry and the reaction conditions such as a reaction solvent, reaction temperature, reaction time, etc. may be selected adequately in consideration of reactants, products, etc.

In an exemplary embodiment, the reaction of the (step a) may be performed at 0-30° C. using an alkali metal carbonate such as sodium bicarbonate as a base and using an acetone solvent.

Step b

In the (step b), the compound represented by Chemical Formula 6 is prepared by reacting the compound represented by Chemical Formula 4 with the aniline derivative represented by Chemical Formula 5.

In an exemplary embodiment, the reaction of the (step b) may be performed overnight under a reflux temperature condition using pyridine as a base and using a tetrahydrofuran solvent.

Step c

In the (step c), the amine compound represented by Chemical Formula 7 is prepared by reducing the nitro compound represented by Chemical Formula 6.

In an exemplary embodiment, the reaction of the (step c) may be performed in the presence of a palladium catalyst and hydrogen gas using a mixture solvent of an alcohol (methanol, ethanol, isopropanol, etc.) and methylene chloride as a reaction solvent. The reaction temperature may be maintained around room temperature (20-30° C.).

Step d-1

In the (step d-1), the compound represented by Chemical Formula 1a is prepared by reacting the amine compound represented by Chemical Formula 7 with the acid chloride derivative represented by Chemical Formula 8-1.

In an exemplary embodiment, the reaction of the (step d-1) may be performed by heating at 40-80° C. using methylene chloride as a solvent.

As a second preparation method, a method for preparing a 6-phenoxypyrimidine derivative wherein the L is —NHC(O)NH— includes:

(step a) a step of preparing a compound represented by Chemical Formula 4 by reacting 2,4-dichloro-5-nitropyrimidine represented by Chemical Formula 2 with a phenol compound represented by Chemical Formula 3;

(step b) a step of preparing a compound represented by Chemical Formula 6 by reacting the compound represented by Chemical Formula 4 with an aniline derivative represented by Chemical Formula 5;

(step c) a step of preparing an amine compound represented by Chemical Formula 7 by reducing the nitro compound represented by Chemical Formula 6; and (step d-2) a step of preparing a compound represented by Chemical Formula 1b by reacting the amine compound represented by Chemical Formula 7 with an isocyanate derivative represented by Chemical Formula 8-2.

[Scheme 2]

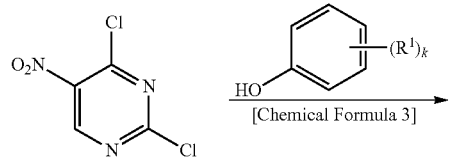

[Chemical Formula 2]

[Chemical Formula 3]

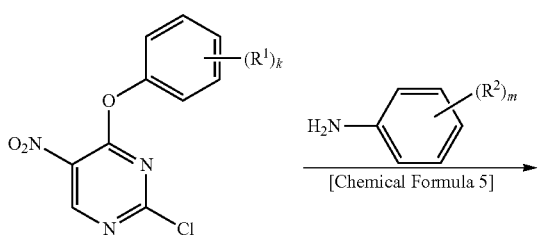

[Chemical Formula 4]

[Chemical Formula 5]

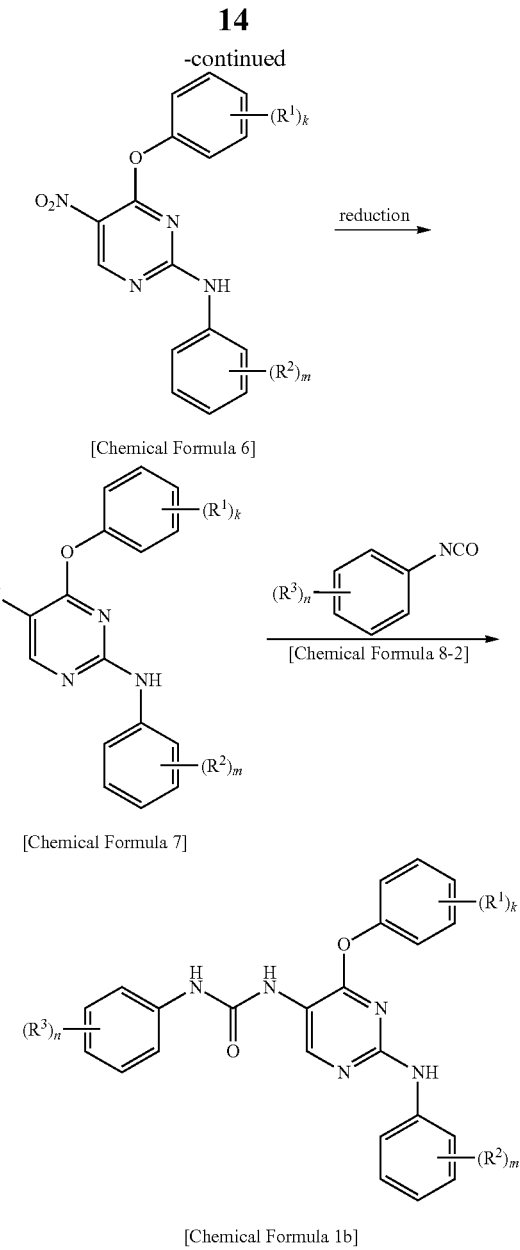

[Chemical Formula 6]

[Chemical Formula 7]

[Chemical Formula 8-2]

[Chemical Formula 1b]

In Scheme 2, $R^1$, $R^2$, $R^3$, k, m and n are the same as defined above in Chemical Formula 1.

The steps of the second preparation method of the present invention illustrated in Scheme 2 are described in more detail.

Steps a-c

The (step a) through the (step c) of the preparation method may be performed according to the first method of Scheme 1.

Step d-2

In the (step d-2), the compound represented by Chemical Formula 1b is prepared by reacting the amine compound represented by Chemical Formula 7 with the isocyanate derivative represented by Chemical Formula 8-2.

In an exemplary embodiment, the reaction of the (step d-2) may be preformed by heating at 40-80° C. using methylene chloride as a solvent.

As a third preparation method, a method for preparing a 6-phenoxypyrimidine derivative wherein the L is —CH═N— includes:

(step a) a step of preparing a compound represented by Chemical Formula 4 by reacting 2,4-dichloro-5-nitropyrimidine represented by Chemical Formula 2 with a phenol compound represented by Chemical Formula 3;

(step b) a step of preparing a compound represented by Chemical Formula 6 by reacting the compound represented by Chemical Formula 4 with an aniline derivative represented by Chemical Formula 5;

(step c) a step of preparing an amine compound represented by Chemical Formula 7 by reducing the nitro compound represented by Chemical Formula 6; and (step d-3) a step of preparing a compound represented by Chemical Formula 1c by reacting the amine compound represented by Chemical Formula 7 with an aldehyde derivative represented by Chemical Formula 8-3.

[Scheme 3]

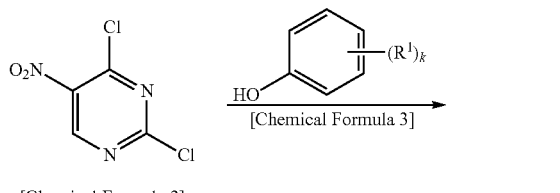

[Chemical Formula 2]     [Chemical Formula 3]

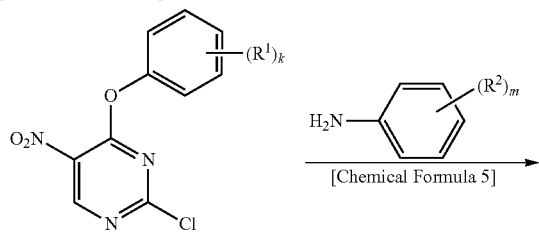

[Chemical Formula 4]     [Chemical Formula 5]

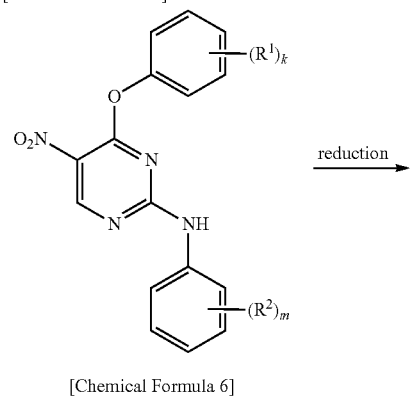

[Chemical Formula 6]

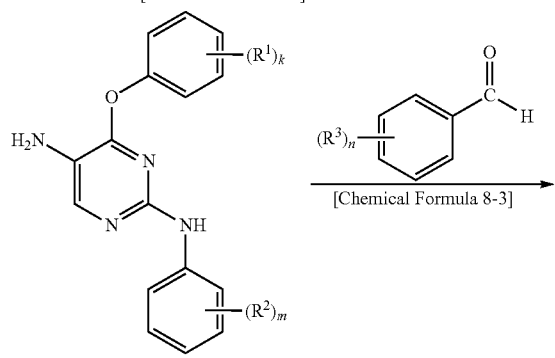

[Chemical Formula 7]     [Chemical Formula 8-3]

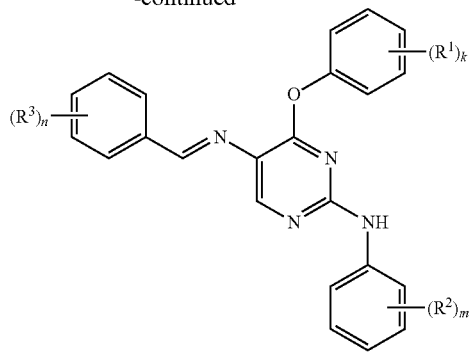

[Chemical Formula 1c]

In Scheme 3, $R^1$, $R^2$, $R^3$, k, m and n are the same as defined above in Chemical Formula 1.

The steps of the third preparation method of the present invention illustrated in Scheme 3 are described in more detail.

Steps a-c

The (step a) through the (step c) of the preparation method may be performed according to the first method of Scheme 1.

Step d-3

In the (step d-3), the compound represented by Chemical Formula 1c is prepared by reacting the amine compound represented by Chemical Formula 7 with the aldehyde derivative represented by Chemical Formula 8-3.

In an exemplary embodiment, the reaction of the (step d-3) may be performed by heating at 40-80° C. using trifluoroacetic acid as a catalyst and using methylene chloride or an alcohol (methanol, ethanol, isopropanol, etc.) as a solvent.

As a fourth preparation method, a method for preparing a 6-phenoxypyrimidine derivative wherein the L is —$CH_2$—NH— includes:

(step a) a step of preparing a compound represented by Chemical Formula 4 by reacting 2,4-dichloro-5-nitropyrimidine represented by Chemical Formula 2 with a phenol compound represented by Chemical Formula 3;

(step b) a step of preparing a compound represented by Chemical Formula 6 by reacting the compound represented by Chemical Formula 4 with an aniline derivative represented by Chemical Formula 5;

(step c) a step of preparing an amine compound represented by Chemical Formula 7 by reducing the nitro compound represented by Chemical Formula 6; and (step d-4) a step of preparing a compound represented by Chemical Formula 1d by reacting the amine compound represented by Chemical Formula 7 with an aldehyde derivative represented by Chemical Formula 8-3 and then reducing the product.

[Scheme 4]

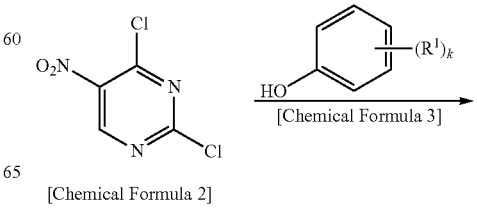

[Chemical Formula 2]     [Chemical Formula 3]

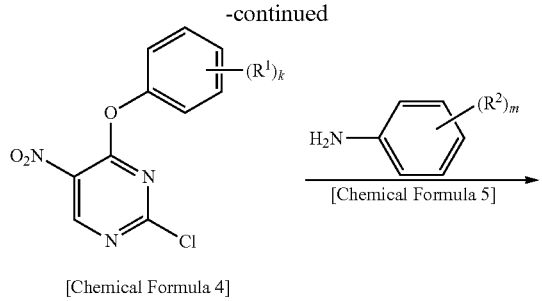

[Chemical Formula 4]

[Chemical Formula 5]

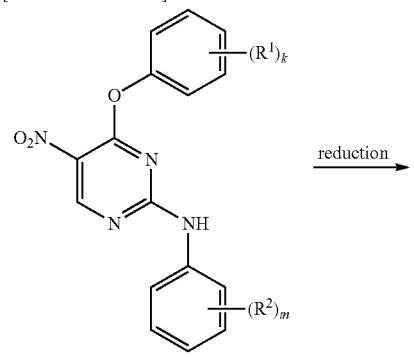

[Chemical Formula 6]

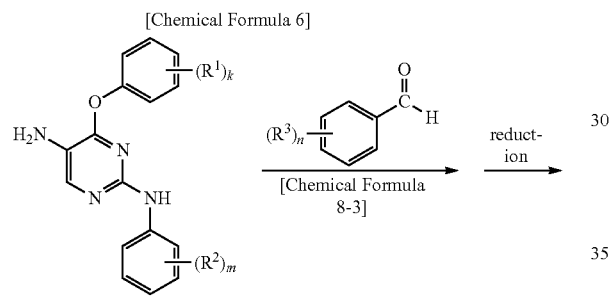

[Chemical Formula 7]

[Chemical Formula 8-3]

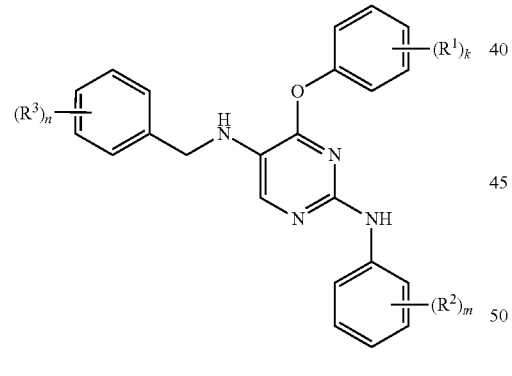

[Chemical Formula 1d]

In Scheme 4, $R^1$, $R^2$, $R^3$, k, m and n are the same as defined above in Chemical Formula 1.

The steps of the fourth preparation method of the present invention illustrated in Scheme 4 are described in more detail.

Steps a-c

The (step a) through the (step c) of the preparation method may be performed according to the first method of Scheme 1.

Step d-4

In the (step d-4), the compound represented by Chemical Formula 1d is prepared by reacting the amine compound represented by Chemical Formula 7 with the aldehyde derivative represented by Chemical Formula 8-3 and then reducing the product.

In an exemplary embodiment, the reaction with the aldehyde derivative in the (step d-4) may be performed by heating at 40-80° C. using trifluoroacetic acid as a catalyst and using methylene chloride or an alcohol (methanol, ethanol, isopropanol, etc.) as a solvent. And, the reduction may be performed by adding a reducing agent such as sodium borohydride ($NaBH_4$) or sodium cyanoborohydride and then stirring at room temperature.

The compounds prepared by the preparation methods of Schemes 1, 2, 3 and 4 may be purified by a general method. For example, the compound may be diluted and washed with an organic solvent and then the organic layer may be concentrated under reduced pressure. If necessary, it may be purified by column chromatography.

Hereinafter, the present invention will be described in more detail through examples and test examples. The following examples are for illustrative purposes only and it will be apparent to those skilled in the art that the scope of this invention is not limited by the examples.

EXAMPLES

Synthesis of Compounds

Example 1. Preparation of N-(2-(3,5-dimethoxyphenylamino)-4-(2-methoxy-4-methylphenoxy)methylphenoxy)-3,5-dimethoxybenzamide

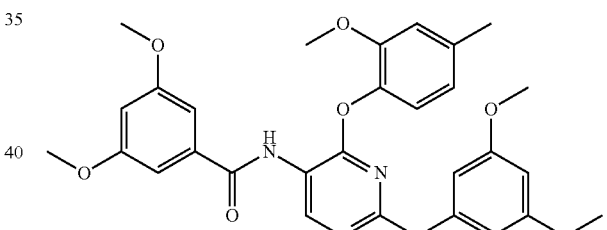

(Step a) Preparation of 2-chloro-4-(2-methoxy-4-methylphenoxy)-5-nitropyrimidine After mixing 2-methoxy-4-methylphenol (0.70 g, 5.15 mmol) in 5 mL of a 1 N sodium bicarbonate aqueous solution, a solution of 2,4-dichloro-5-nitropyrimidine (1.00 g, 5.15 mmol) dissolved in 20 mL of an acetone solvent was slowly added at 0° C. After the addition was completed, the temperature of the reaction mixture was raised to room temperature and a reaction was performed at room temperature for 2 hours. The final mixture was evaporated under reduced pressure and the residue was extracted with ethyl acetate and 1 N NaOH (3 times×100 mL). The organic solvent layer was extracted continuously with water (3 times×200 mL) and brine (3 times×200 mL) and the organic solvent was dried with anhydrous magnesium sulfate and then filtered. After evaporating the solvent under reduced pressure, the residue was purified by column chromatography using a 10-20% mixture of ethyl acetate and hexane as a mobile phase. The target compound was obtained as a pale yellow solid.

¹H NMR (400 MHz, CDCl₃) δ 9.18 (s, 1H), 7.07 (d, 1H, J=7.8 Hz), 6.86-6.84 (m, 2H), 3.78 (s, 3H), 2.43 (s, 3H).

(Step b) Preparation of 4-(2-methoxy-4-methylphenoxy)-N-(3,5-dimethoxyphenyl)-5-nitropyrimidin-2-amine After adding 3,5-dimethoxyaniline (0.15 g, 1 mmol) and pyridine (0.08 g, 1 mmol) to 5 mL of a tetrahydrofuran solvent, 2-chloro-4-(2-methoxy-4-methylphenoxy)-5-nitropyrimidine (0.30 g, 1 mmol) was added at 0° C. After raising the temperature of the reaction mixture to room temperature, the mixture was heated at 80° C. for 4 hours under reflux. After evaporating the solvent under reduced pressure, the residue was purified by column chromatography using a 30-50% mixture of ethyl acetate and hexane as a mobile phase. The target compound was obtained as a reddish orange solid.

¹H NMR (400 MHz, DMSO-d₆) δ 10.59 (s, 1H), 9.19 (s, 1H), 7.13 (d, 1H, J=8.0 Hz), 7.04 (s, 1H), 6.83 (d, 1H, J=7.9 Hz), 6.57 (s, 1H), 6.18 (s, 1H), 3.71 (s, 3H), 3.60 (s, 6H), 2.38 (s, 3H).

(Step c) Preparation of 4-(2-methoxy-4-methylphenoxy)-N-(3,5-dimethoxyphenyl)pyrimidine-2,5-diamine After dissolving 4-(2-methoxy-4-methylphenoxy)-N-(3,5-dimethoxyphenyl)-5-nitropyrimidin-2-amine (0.44 g, 1 mmol) in a mixture solvent of 50 mL of methanol and 5 mL of methylene chloride, 10% Pd/C catalyst was added. The reaction mixture was reacted at room temperature for 12 hours under a hydrogen gas condition. After the reaction was completed, the catalyst was filtered using celite. The target compound was obtained by evaporating the solvent under reduced pressure.

¹H NMR (400 MHz, DMSO-d₆) δ 8.70 (s, 1H), 7.83 (s, 1H), 7.03 (d, 1H, J=7.9 Hz), 6.98 (s, 1H), 6.78 (d, 1H, J=7.9 Hz), 6.71 (s, 2H), 5.90 (s, 1H), 4.59 (s, 2H), 3.69 (s, 3H), 3.54 (s, 6H), 2.34 (s, 3H).

(Step d-1) Preparation of N-(2-(3,5-dimethoxyphenylamino)-4-(2-methoxy-4-methylphenoxy)methylphenoxy)-3,5-dimethoxybenzamide After dissolving 4-(2-methoxy-4-methylphenoxy)-N-(3,5-dimethoxyphenyl)pyrimidine-2,5-diamine (0.04 g, 0.1 mmol) in 5 mL of methylene chloride, 3,5-dimethoxybenzoic acid chloride (0.02 g, 0.11 mmol) was added at 0° C. After raising the temperature of the reaction mixture to room temperature, the mixture was heated at 50° C. for 12 hours under reflux. After the reaction was completed, a residue was obtained by concentrating under reduced pressure. The residue was purified by column chromatography using a mixture of ethyl acetate and n-hexane as a mobile phase. The target compound was obtained with a yield of 53%.

¹H NMR (400 MHz, DMSO-d₆) δ 9.89 (s, 1H), 9.43 (s, 1H), 8.41 (s, 1H), 7.17 (d, 2H, J=2.2 Hz), 7.01-6.99 (m, 2H), 6.79-6.75 (m, 3H), 6.71 (t, 1H, J=2.2 Hz), 6.02 (t, 1H, J=2.2 Hz), 3.81 (s, 6H), 3.68 (s, 3H), 3.56 (s, 6H), 2.34 (s, 3H).

Example 2. Preparation of 3,5-dimethoxy-N-(4-(2-methoxy-4-methylphenoxy)-2-(4-morpholinophenylamino)methylphenoxy)benzamide

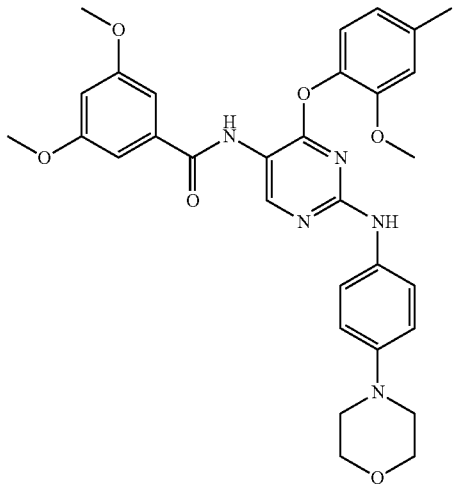

(Step a) Preparation of 2-chloro-4-(2-methoxy-4-methylphenoxy)-5-nitropyrimidine After mixing 2-methoxy-4-methylphenol (0.71 g, 5.15 mmol) in 5 mL of a 1 N sodium bicarbonate aqueous solution, a solution of 2,4-dichloro-5-nitropyrimidine (1.00 g, 5.15 mmol) dissolved in 20 mL of an acetone solvent was slowly added at 0° C. After the addition was completed, the temperature of the reaction mixture was raised to room temperature and a reaction was performed at room temperature for 2 hours. The final mixture was evaporated under reduced pressure and the residue was extracted with ethyl acetate and 1 N NaOH (3 times×100 mL). The organic solvent layer was extracted continuously with water (3 times×200 mL) and brine (3 times×200 mL) and the organic solvent was dried with anhydrous magnesium sulfate and then filtered. After evaporating the solvent under reduced pressure, the residue was purified by column chromatography using a 10-20% mixture of ethyl acetate and hexane as a mobile phase. The target compound was obtained as a pale yellow solid.

¹H NMR (400 MHz, CDCl₃) δ 9.18 (s, 1H), 7.07 (d, 1H, J=7.8 Hz), 6.86-6.84 (m, 2H), 3.78 (s, 3H), 2.43 (s, 3H).

(Step b) Preparation of 4-(2-methoxy-4-methylphenoxy)-N-(4-morpholinophenyl)-5-nitropyrimidin-2-amine After adding 3,5-dimethoxyaniline (0.15 g, 1.00 mmol) and pyridine (0.08 g, 1 mmol) to 5 mL of a tetrahydrofuran solvent, 2-chloro-4-(2-methoxy-4-methylphenoxy)-5-nitropyrimidine (0.30 g, 1.00 mmol) was added at 0° C. After raising the temperature of the reaction mixture to room temperature, the mixture was heated at 80° C. for 4 hours under reflux. After evaporating the solvent under reduced pressure, the residue was purified by column chromatography using a 30-50% mixture of ethyl acetate and hexane as a mobile phase. The target compound was obtained as a reddish orange solid.

$^1$H NMR (400 MHz, DMSO-d$_6$) δ 10.63 (s, 1H), 9.13 (s, 1H), 7.13-7.08 (m, 3H), 6.87 (d, 2H, J=8.0 Hz), 6.57 (d, 2H, J=8.7 Hz), 3.72 (t, 4H, J=4.6 Hz), 3.69 (s, 3H), 3.00 (t, 4H, J=4.4 Hz), 2.43 (s, 3H).

(Step c) Preparation of 4-(2-methoxy-4-methylphenoxy)-N2-(4-morpholinophenyl)pyrimidine-2,5-diamine After dissolving 4-(2-methoxy-4-methylphenoxy)-N-(4-morpholinophenyl)-5-nitropyrimidin-2-amine (0.44 g, 1 mmol) in a mixture solvent of 50 mL of methanol and 5 mL of methylene chloride, 10% Pd/C catalyst was added. The reaction mixture was reacted at room temperature for 12 hours under a hydrogen gas condition. After the reaction was completed, the catalyst was filtered using celite. The target compound was obtained by evaporating the solvent under reduced pressure.

$^1$H NMR (400 MHz, DMSO-d$_6$) δ 8.59 (s, 1H), 7.79 (s, 1H), 7.21 (d, 2H, J=9.0 Hz), 7.04-7.01 (m, 2H), 6.81 (dd, 1H, J=8.0, 1.2 Hz), 6.62 (d, 2H, J=9.0 Hz), 4.79 (s, 2H), 3.72-3.68 (m, 7H), 2.93 (t, 4H, J=4.8 Hz), 2.39 (s, 3H).

(Step d-1) Preparation of 3,5-dimethoxy-N-(4-(2-methoxy-4-methylphenoxy)-2-(4-morpholinophenylamino)methylphenoxy)benzamide After dissolving 4-(2-methoxy-4-methylphenoxy)-N2-(4-morpholinophenyl)pyrimidine-2,5-diamine (0.04 g, 0.10 mmol) in 5 mL of methylene chloride, 3,5-dimethoxybenzoic acid chloride (0.02 g, 0.11 mmol) was added at 0° C. After raising the temperature of the reaction mixture to room temperature, the mixture was heated at 50° C. for 12 hours under reflux. After the reaction was completed, a residue was obtained by concentrating under reduced pressure. The residue was purified by column chromatography using a mixture of ethyl acetate and n-hexane as a mobile phase. The target compound was obtained with a yield of 53%.

$^1$H NMR (400 MHz, DMSO-d$_6$) δ 9.23 (s, 1H), 8.01 (s, 1H), 7.14 (d, 2H, J=8.9 Hz), 7.01 (d, 1H, J=7.7 Hz), 6.97 (d, 2H, J=2.2 Hz), 6.78-6.76 (m, 3H), 6.64 (d, 2H, J=9.0 Hz), 6.56 (t, 1H, J=2.2 Hz), 3.80-3.77 (m, 10H), 3.66 (s, 3H), 2.99 (t, 4H, J=4.8 Hz), 2.37 (s, 3H).

Example 3. Preparation of 1-(3,5-dimethoxyphenyl)-3-(2-(3,5-dimethoxyphenylamino)-4-(2-methoxy-4-methylphenoxy)methylphenoxy)urea

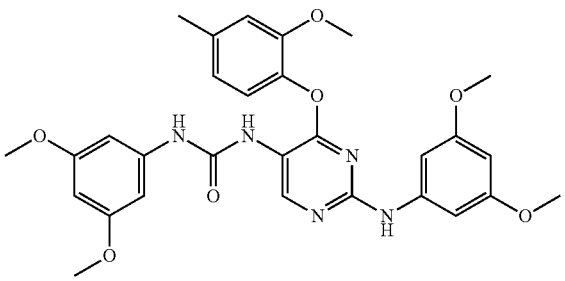

After dissolving 4-(2-methoxy-4-methylphenoxy)-N-(3,5-dimethoxyphenyl)pyrimidine-2,5-diamine (0.04 g, 0.10 mmol) in 5 mL of methylene chloride, 1-isocyanato-3,5-dimethoxybenzene (0.02 g, 0.11 mmol) was added at 0° C. After raising the temperature of the reaction mixture to room temperature, the mixture was heated at 50° C. for 12 hours under reflux. After the reaction was completed, a residue was obtained by concentrating under reduced pressure. The residue was purified by column chromatography using a mixture of ethyl acetate and n-hexane as a mobile phase to obtain the target compound.

$^1$H NMR (400 MHz, DMSO-d$_6$) δ 9.24 (s, 1H), 9.12 (s, 1H), 8.88 (s, 1H), 8.31 (s, 1H), 7.12 (d, 1H, J=8.0 Hz), 7.02 (d, 1H, J=1.5 Hz), 6.81 (dd, 1H, J=7.5, 1.5 Hz), 6.72 (d, 2H, J=2.1 Hz), 6.67-6.66 (m, 2H), 6.15 (t, 1H, J=2.2 Hz), 5.97 (t, 1H, J=2.2 Hz), 3.72 (s, 6H), 3.71 (s, 3H), 3.55 (s, 6H), 2.36 (s, 3H).

6-Phenoxypyrimidine compounds represented by Chemical Formula 1b were synthesized in the same manner as in Example 3. Their structures and $^1$H NMR data are described in Table 1.

TABLE 1

| Example | Compound structure | $^1$H NMR (ppm) δ |
| --- | --- | --- |
| 4 | 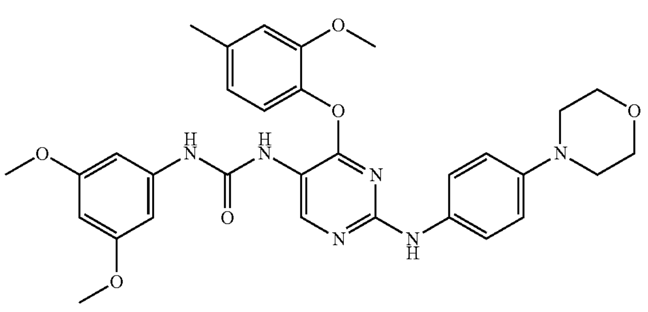 [SMILES: COc1cc(NC(=O)Nc2cnc(Nc3ccc(N4CCOCC4)cc3)nc2Oc2ccc(C)cc2OC)cc(OC)c1] | 9.11 (s, 1H), 9.08 (s, 1H), 8.76 (s, 1H), 8.25 (s, 1H), 7.22 (d, 2H, J = 9.0 Hz), 7.10 (d, 1H, J = 7.9 Hz), 7.07 (d, 1H, J = 1.6 Hz), 6.84 (dd, 1H, J = 8.0, 1.2 Hz), 6.66 (d, 2H, J = 2.2 Hz), 6.62 (d, 2H, J = 9.1 Hz), 6.14 (t, 1H, J = 2.2 Hz), 3.72-3.71 (m, 13H), 2.95 (t, 4H, J = 4.6 Hz), 2.40 (s, 3H). |

TABLE 1-continued

| Example | Compound structure | $^1$H NMR (ppm) δ |
|---|---|---|
| 5 | 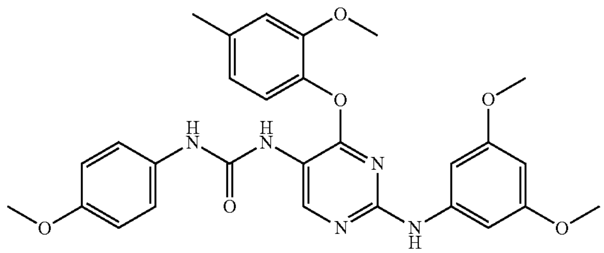 | 9.21 (s, 1H), 8.92 (s, 1H), 8.89 (s, 1H), 8.24 (s, 1H), 7.35 (d, 2H, J = 9.0 Hz), 7.12 (d, 1H, J = 8.0 Hz), 7.01 (d, 1H, J = 1.5 Hz), 6.87 (d, 2H, J = 9.0 Hz), 6.81 (dd, 1H, J = 8.0, 1.2 Hz), 6.73 (d, 2H, J = 2.2 Hz), 5.97 (d, 1H, J = 2.2 Hz), 3.72 (s, 3H), 3.71 (s, 3H), 3.55 (s, 6H), 2.36 (s, 3H). |
| 6 | 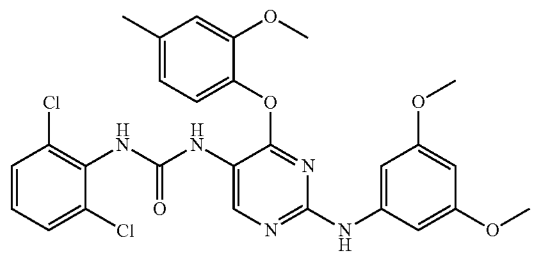 [SMILES: COc1cc(Nc2ncc(NC(=O)Nc3c(Cl)cccc3Cl)c(Oc3ccc(C)cc3OC)n2)cc(OC)c1] | 9.23 (s, 1H), 8.88 (s, 1H), 8.71 (s, 1H), 8.64 (s, 1H), 7.54 (d, 2H, J = 8.0 Hz), 7.32 (t, 1H, J = 7.9 Hz), 7.15 (d, 1H, J = 8.0 Hz), 7.03 (d, 1H, J = 1.6 Hz), 6.82 (dd, 1H, J = 8.8, 1.2 Hz), 6.72 (d, 2H, J = 2.2 Hz), 5.97 (t, 1H, J = 2.2 Hz), 3.73 (s, 3H), 3.55 (s, 6H), 2.36 (s, 3H). |
| 7 | 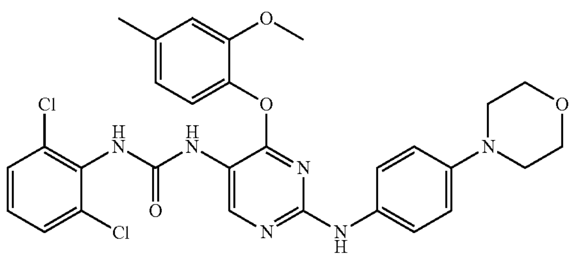 [SMILES: COc1cc(C)ccc1Oc1nc(Nc2ccc(N3CCOCC3)cc2)ncc1NC(=O)Nc1c(Cl)cccc1Cl] | 9.09 (s, 1H), 8.77 (s, 1H), 8.65 (s, 1H), 8.56 (s, 1H), 7.54 (d, 2H, J = 8.1 Hz), 7.31 (t, 1H, J = 7.8 Hz), 7.22 (d, 2H, J = 9.0 Hz), 7.13 (d, 1H, J = 7.9 Hz), 7.09 (d, 1H, J = 1.5 Hz), 6.85 (dd, 1H, J = 8.0, 1.2 Hz), 6.62 (d, 2H, J = 9.1 Hz), 3.73-3.73 (m, 7H), 2.95 (t, 4H, J = 4.6 Hz), 2.40 (s, 3H). |
| 8 | 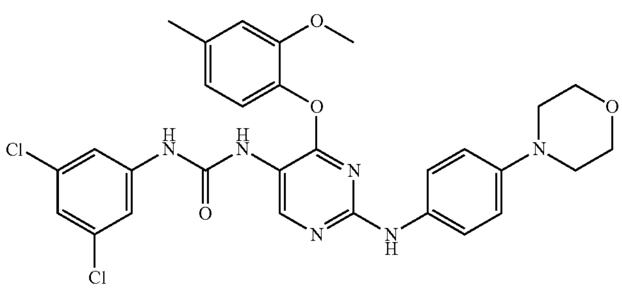 [SMILES: COc1cc(C)ccc1Oc1nc(Nc2ccc(N3CCOCC3)cc2)ncc1NC(=O)Nc1cc(Cl)cc(Cl)c1] | 9.39 (s, 1H), 9.18 (s, 1H), 8.71 (s, 1H), 8.43 (s, 1H), 7.52 (d, 2H, J = 1.8 Hz), 7.23 (d, 2H, J = 8.8 Hz), 7.17 (t, 1H, J = 1.8 Hz), 7.10-7.08 (m, 2H), 6.84 (dd, 1H, J = 8.0, 1.1 Hz), 6.63 (d, 2H, J = 9.0 Hz), 3.73-3.70 (m, 7H), 2.96 (t, 4H, J = 4.6 Hz), 2.40 (s, 3H). |
| 9 | 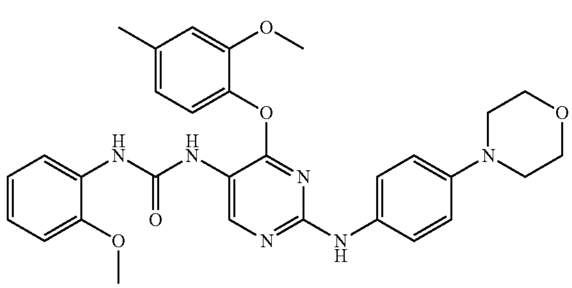 [SMILES: COc1ccccc1NC(=O)Nc1cnc(Nc2ccc(N3CCOCC3)cc2)nc1Oc1ccc(C)cc1OC] | 9.09 (s, 1H), 8.99 (s, 1H), 8.79-8.76 (m, 2H), 8.13 (dd, 1H, J = 7.8, 1.7 Hz), 7.22 (d, 2H, J = 8.9 Hz), 7.11-7.08 (m, 2H), 7.01 (dd, 1H, J = 8.1, 1.6 Hz), 6.96-6.83 (m, 3H), 6.62 (d, 2H, J = 9.1 Hz), 3.86 (s, 3H), 3.74-3.71 (m, 7H), 2.95 (t, 4H, J = 4.6 Hz), 2.40 (s, 3H). |

TABLE 1-continued

| Example | Compound structure | $^1$H NMR (ppm) δ |
|---|---|---|
| 10 | 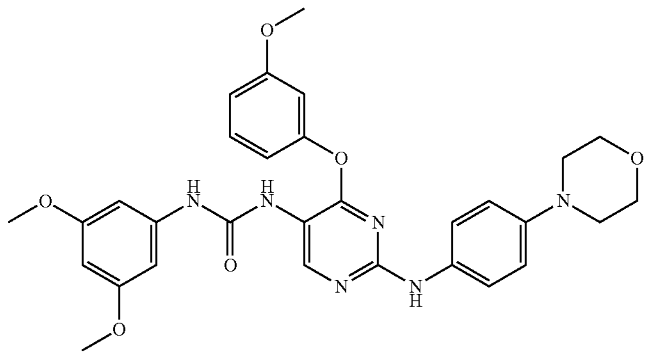 [SMILES: COc1cc(NC(=O)Nc2cnc(Nc3ccc(N4CCOCC4)cc3)nc2Oc2cccc(OC)c2)cc(OC)c1] | 9.20 (s, 1H), 9.13 (s, 1H), 8.74 (s, 1H), 8.21 (s, 1H), 7.40 (t, 1H, J = 8.9 Hz), 7.32 (d, 2H, J = 8.9 Hz), 6.93-6.90 (m, 2H), 6.86 (dd, 1H, J = 1.6, 7.5 Hz), 6.68-6.65 (m, 4H), 6.14 (t, 1H, J = 2.1 Hz), 3.77 (s, 3H), 3.72-3.71 (m, 10H), 2.95 (t, 4H, J = 4.5 Hz). |
| 11 | 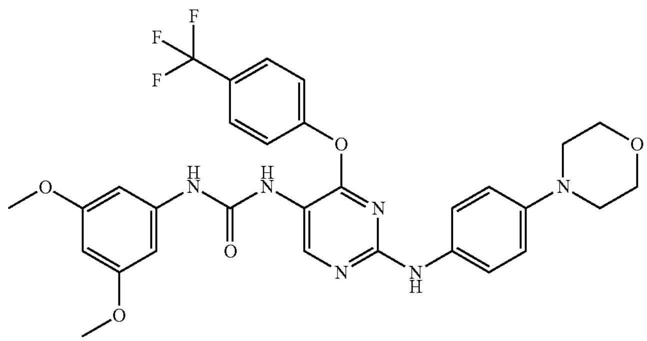 [SMILES: COc1cc(NC(=O)Nc2cnc(Nc3ccc(N4CCOCC4)cc3)nc2Oc2ccc(C(F)(F)F)cc2)cc(OC)c1] | 9.27 (s, 1H), 9.11 (s, 1H), 8.76 (s, 1H), 8.28 (s, 1H), 7.90 (d, 2H, J = 8.6 Hz), 7.54 (d, 2H, J = 8.4 Hz), 7.19 (d, 2H, J = 8.5 Hz), 6.68 (d, 2H, J = 2.1 Hz), 6.62 (d, 2H, J = 8.9 Hz), 6.14 (t, 1H, J = 2.1 Hz), 3.71-3.69 (m, 10H), 2.93 (t, 4H, J = 4.4 Hz). |
| 12 | 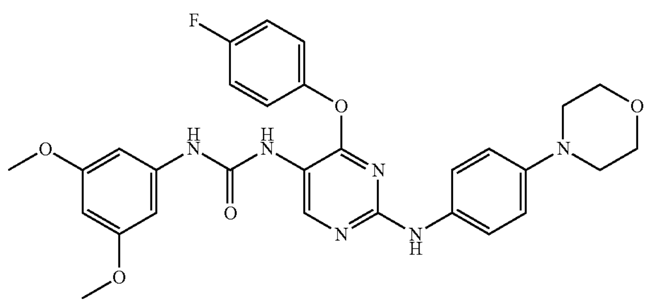 [SMILES: COc1cc(NC(=O)Nc2cnc(Nc3ccc(N4CCOCC4)cc3)nc2Oc2ccc(F)cc2)cc(OC)c1] | 9.18 (s, 1H), 9.08 (s, 1H), 8.74 (s, 1H), 8.21 (s, 1H), 7.34 (d, 4H, J = 6.5 Hz), 7.27 (d, 2H, J = 8.9 Hz), 6.68-6.66 (m, 4H), 6.14 (t, 1H, J = 2.2 Hz), 3.72-3.70 (m, 10H), 2.95 (t, 4H, J = 4.6 Hz). |
| 13 | 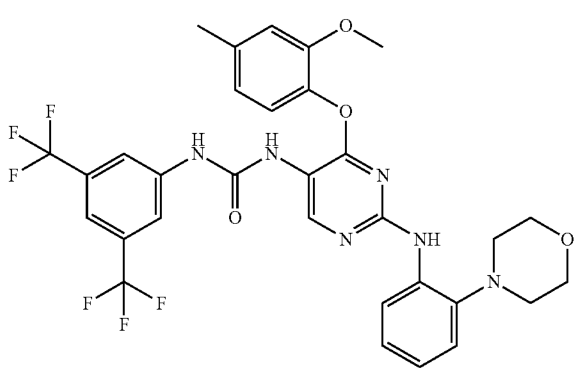 [SMILES: COc1cc(C)ccc1Oc1nc(Nc2ccccc2N2CCOCC2)ncc1NC(=O)Nc1cc(C(F)(F)F)cc(C(F)(F)F)c1] | 9.72 (s, 1H), 9.21 (s, 1H), 8.69 (s, 1H), 8.50 (s, 1H), 8.12 (s, 2H), 7.65 (s, 1H), 7.23 (d, 2H, J = 8.8 Hz), 7.09-7.07 (m, 2H), 6.84 (dd, 1H, J = 1.0, 8.0 Hz), 6.63 (d, 2H, J = 9.0 Hz), 3.73-3.70 (m, 7H), 2.96 (t, 4H, J = 4.6 Hz), 2.40 (s, 3H). |

TABLE 1-continued

| Example | Compound structure | $^1$H NMR (ppm) δ |
|---|---|---|
| 14 | 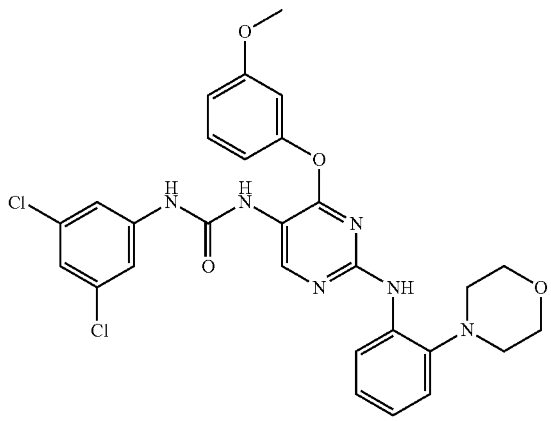 [SMILES: COc1cccc(Oc2nc(Nc3ccccc3N3CCOCC3)ncc2NC(=O)Nc2cc(Cl)cc(Cl)c2)c1] | 9.48 (s, 1H), 9.25 (s, 1H), 8.69 (s, 1H), 8.46 (s, 1H), 7.56 (s, 2H), 7.42 (t, 1H, J = 8.1 Hz), 7.33 (d, 2H, J = 8.2 Hz), 7.18 (s, 1H), 6.94-6.86 (m, 3H), 6.68 (d, 2H, J = 8.8 Hz), 3.79 (s, 3H), 3.74 (s, 4H), 2.98 (s, 4H). |
| 15 | 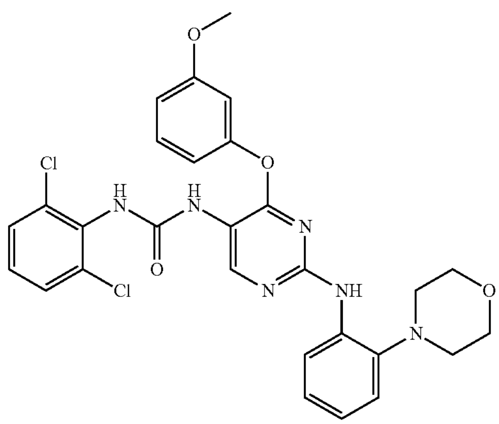 [SMILES: COc1cccc(Oc2nc(Nc3ccccc3N3CCOCC3)ncc2NC(=O)Nc2c(Cl)cccc2Cl)c1] | 9.18 (s, 1H), 8.73 (s, 2H), 8.56 (s, 1H), 7.53 (d, 2H, J = 8.0 Hz), 7.41 (t, 1H, J = 8.0 Hz), 7.33-7.31 (m, 3H), 6.97-6.88 (m, 3H), 6.66 (d, 2H, J = 8.8 Hz), 3.78 (s, 3H), 3.72 (s, 4H), 2.96 (s, 4H). |

Example 16. Preparation of (E)-5-((3,5-dimethoxybenzylidene)amino)-4-(2-methoxy-4-methylphenoxy)-N-(4-morpholinophenyl)pyrimidin-2-amine

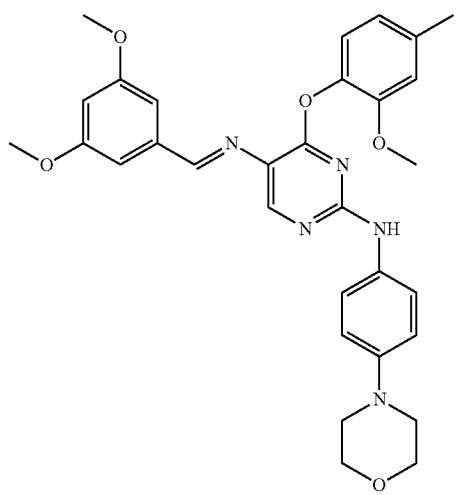

After dissolving 4-(2-methoxy-4-methylphenoxy)-N2-(4-morpholinophenyl)pyrimidine-2,5-diamine (0.08 g, 0.20 mmol) in 5 mL of anhydrous isopropanol and adding a catalytic amount of trifluoroacetic acid, 3,5-dimethoxybenzaldehyde (0.04 g, 0.22 mmol) was added. The reaction mixture heated at 80° C. for 12 hours under reduced and then neutralized by adding 2 drops of triethylamine. After the reaction was completed, a residue was obtained by concentrating under reduced pressure. The residue was purified by chromatography using neutral alumina as a stationary phase and using a mixture of ethyl acetate and n-hexane as a mobile phase. The target compound was obtained with a yield of 20%.

$^1$H NMR (400 MHz, DMSO-d$_6$): δ 9.39 (s, 1H), 8.81 (s, 1H), 8.32 (s, 1H), 7.22 (d, 2H, J=8.5 Hz), 7.11-7.08 (m, 4H), 6.84 (d, 1H, J=8.1 Hz), 6.65-6.61 (m, 3H), 3.81 (s, 6H), 3.72 (t, 4H, J=4.7 Hz), 3.70 (s, 3H), 2.97 (t, 4H, J=4.6 Hz), 2.40 (s, 3H).

6-Phenoxypyrimidine derivative compounds were synthesized in the same manner as in Example 16. Their structures and $^1$H NMR data are described in Table 2.

TABLE 2

| Example | Compound structure | ¹H NMR (ppm) δ |
| --- | --- | --- |
| 17 | 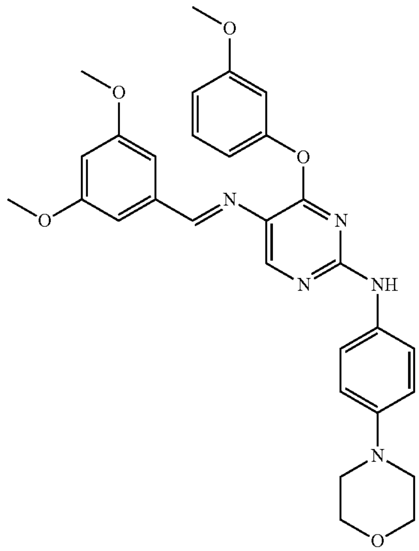 [SMILES: COc1cc(/C=N/c2cnc(Nc3ccc(N4CCOCC4)cc3)nc2Oc2cccc(OC)c2)cc(OC)c1] | 9.46 (s, 1H), 8.80 (s, 1H), 8.36 (s, 1H), 7.40 (t, 1H, J = 8.6 Hz), 7.32 (d, 2H, J = 8.0 Hz), 7.08 (d, 2H, J = 2.3 Hz), 6.93-6.91 (m, 2H), 6.87 (dd, 1H, J = 7.6, 1.5 Hz), 6.68-6.64 (m, 3H), 3.81 (s, 6H), 3.77 (s, 3H), 3.72 (t, 4H, J = 4.4 Hz), 2.96 (t, 4H, J = 4.8 Hz). |
| 18 | 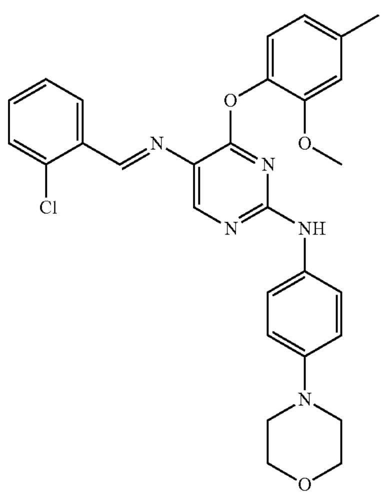 [SMILES: COc1cc(C)ccc1Oc1nc(Nc2ccc(N3CCOCC3)cc2)ncc1/N=C/c1ccccc1Cl] | 9.40 (s, 1H), 8.32-8.29 (m, 2H), 7.42-7.34 (m, 3H), 7.19 (d, 2H, J = 8.7 Hz), 7.09 (d, 1H, J = 7.8 Hz), 6.97 (s, 1H), 6.86-6.83 (m, 2H), 6.69 (d, 2H, J = 8.9 Hz), 3.86 (t, 4H, J = 4.6 Hz), 3.73 (s, 3H), 3.06 (t, 4H, J = 4.8 Hz), 2.45 (s, 3H). |
| 19 | 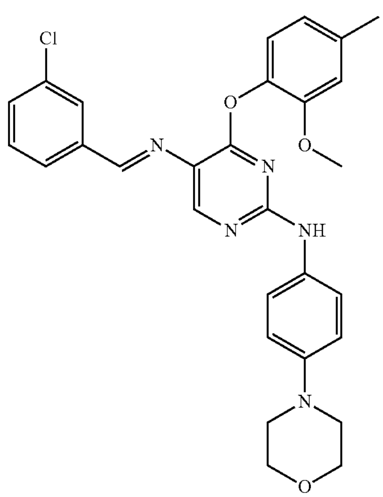 [SMILES: COc1cc(C)ccc1Oc1nc(Nc2ccc(N3CCOCC3)cc2)ncc1/N=C/c1cccc(Cl)c1] | 9.46 (s, 1H), 8.91 (s, 1H), 8.38 (s, 1H), 7.96 (s, 1H), 7.87 (d, 1H, J = 7.1 Hz), 7.59-7.53 (m, 2H), 7.22 (d, 2H, J = 8.0 Hz), 7.11-7.08 (m, 2H), 6.84 (d, 1H, J = 8.2 Hz), 6.62 (d, 2H, J = 8.2 Hz), 3.73-3.69 (m, 7H), 2.97 (t, 4H, J = 4.8 Hz), 2.41 (s, 3H). |

TABLE 2-continued
| Example | Compound structure | $^1$H NMR (ppm) δ |
|---|---|---|
| 20 | 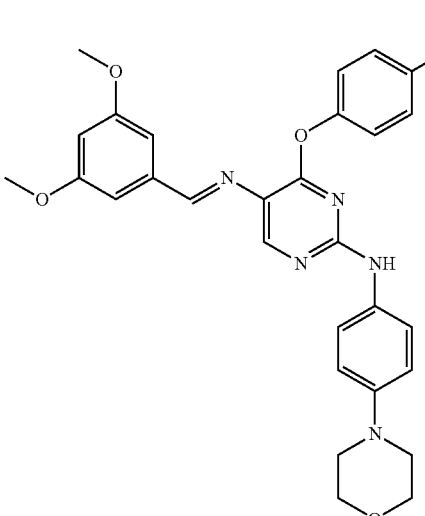 | 9.53 (s, 1H), 8.82 (s, 1H), 8.42 (s, 1H), 7.89 (d, 2H, J = 8.6 Hz), 7.55 (d, 2H, J = 8.4 Hz), 7.20 (s, 2H), 7.08 (d, 2H, J = 2.2 Hz), 6.65-6.61 (m, 3H), 3.80 (s, 6H), 3.71 (t, 4H, J = 4.3 Hz), 2.94 (t, 4H, J = 4.5 Hz). |
| 21 | 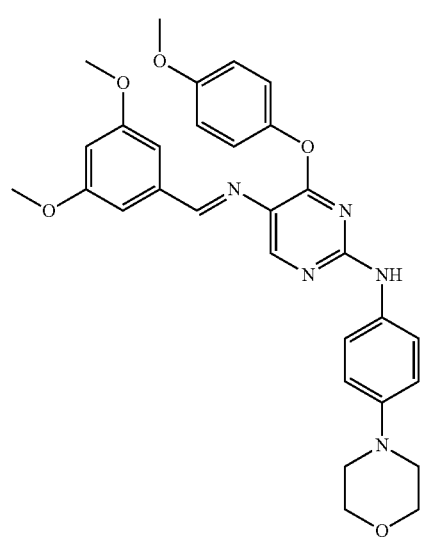 [SMILES: COc1ccc(Oc2nc(Nc3ccc(N4CCOCC4)cc3)ncc2/N=C/c2cc(OC)cc(OC)c2)cc1] | 9.40 (s, 1H), 8.81 (s, 1H), 8.33 (s, 1H), 7.24 (d, 2H, J = 8.1 Hz), 7.20 (d, 2H, J = 9.0 Hz), 7.09 (d, 2H, J = 2.3 Hz), 7.04 (d, 2H, J = 9.0 Hz), 6.65-6.64 (m, 3H), 3.82 (s, 3H), 3.81 (s, 6H), 3.72 (t, 4H, J = 4.4 Hz), 2.96 (t, 4H, J = 4.7 Hz). |
| 22 | 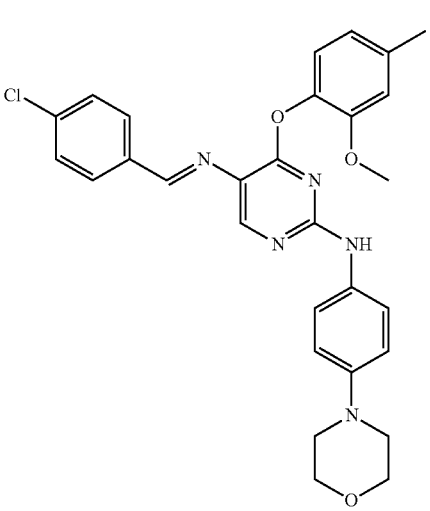 [SMILES: COc1cc(C)ccc1Oc1nc(Nc2ccc(N3CCOCC3)cc2)ncc1/N=C/c1ccc(Cl)cc1] | 9.43 (s, 1H), 8.90 (s, 1H), 8.37 (s, 1H), 7.94 (d, 2H, J = 8.6 Hz), 7.58 (d, 2H, J = 8.5 Hz), 7.22 (d, 2H, J = 8.0 Hz), 7.10-7.07 (m, 2H), 6.84 (d, 1H, J = 7.0 Hz), 6.62 (d, 2H, J = 8.6 Hz), 3.72 (t, 4H, J = 4.5 Hz), 3.69 (s, 3H), 2.97 (t, 4H, J = 4.9 Hz). |

TABLE 2-continued

| Example | Compound structure | ¹H NMR (ppm) δ |
| --- | --- | --- |
| 23 | 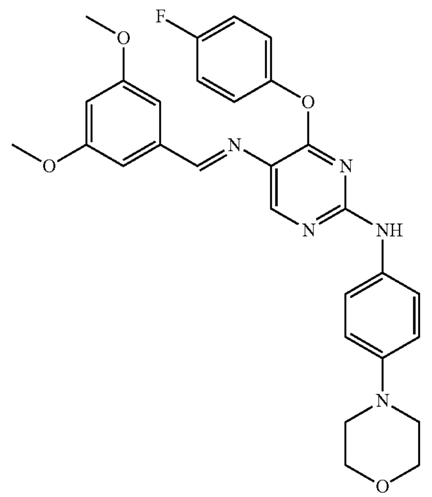 [SMILES: COc1cc(/C=N/c2cnc(Nc3ccc(N4CCOCC4)cc3)nc2Oc2ccc(F)cc2)cc(OC)c1] | 9.46 (s, 1H), 8.82 (s, 1H), 8.38 (s, 1H), 7.37-7.35 (m, 4H), 7.28 (d, 2H, J = 7.8 Hz), 7.10 (d, 2H, J = 2.3 Hz), 6.69-6.65 (m, 3H), 3.82 (s, 6H), 3.73 (t, 4H, J = 4.5 Hz), 2.98 (t, 4H, J = 4.6 Hz). |
| 24 | 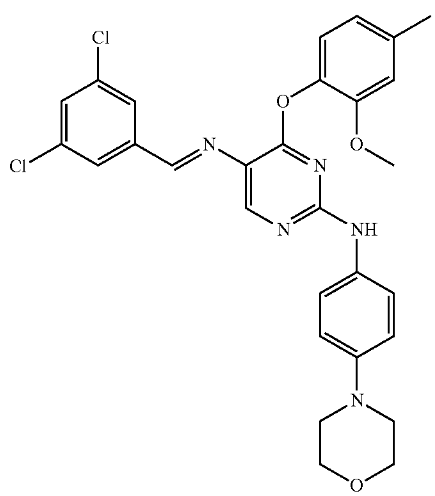 [SMILES: COc1cc(C)ccc1Oc1nc(Nc2ccc(N3CCOCC3)cc2)ncc1/N=C/c1cc(Cl)cc(Cl)c1] | 8.89 (s, 1H), 8.26 (s, 1H), 7.72 (d, 2H, J = 1.8 Hz), 7.34 (t, 1H, J = 1.8 Hz), 7.10 (d, 2H, J = 8.0 Hz), 6.99 (d, 1H, J = 7.8 Hz), 6.79-6.77 (m, 2H), 6.63 (d, 2H, J = 7.2 Hz), 3.80 (t, 4H, J = 4.4 Hz), 3.66 (s, 3H), 3.00 (s, 4H), 2.39 (s, 3H). |
| 25 | 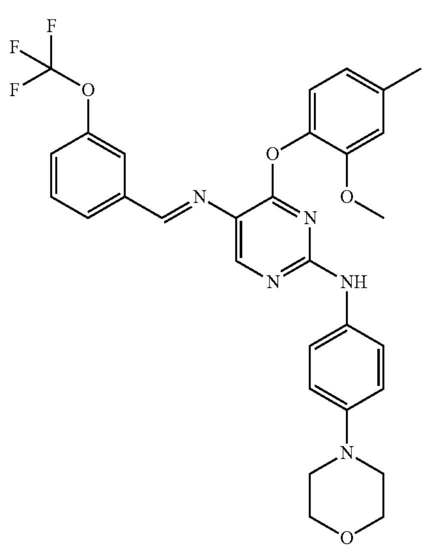 [SMILES: COc1cc(C)ccc1Oc1nc(Nc2ccc(N3CCOCC3)cc2)ncc1/N=C/c1cccc(OC(F)(F)F)c1] | 9.06 (s, 1H), 8.37 (s, 1H), 7.86-7.84 (m, 2H), 7.50 (t, 1H, J = 8.0 Hz), 7.34-7.31 (m, 1H), 7.21 (d, 2H, J = 8.7 Hz), 7.10 (d, 1H, J = 7.8 Hz), 7.05 (s, 1H), 6.89-6.87 (m, 2H), 6.72 (d, 2H, J = 8.9 Hz), 3.89 (t, 4H, J = 4.6 Hz), 3.76 (s, 3H), 3.09 (t, 4H, J = 4.7 Hz), 2.48 (s, 3H). |

TABLE 2-continued
| Example | Compound structure | $^1$H NMR (ppm) δ |
|---|---|---|
| 26 | 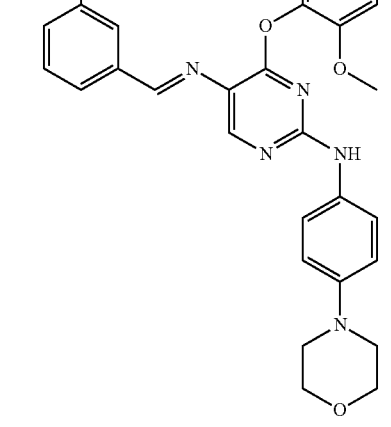 | 8.94 (s, 1H), 8.30 (s, 1H), 7.54 (s, 1H), 7.44 (d, 1H, J = 7.5 Hz), 7.36 (t, 1H, J = 7.8 Hz), 7.20 (d, 2H, J = 8.7 Hz), 7.10 (d, 1H, J = 7.8 Hz), 7.01 (dd, 1H, J = 7.8, 1.9 Hz), 6.88-6.86 (m, 2H), 6.71 (d, 2H, J = 8.8 Hz), 4.72-4.66 (m, 1H), 3.88 (t, 4H, J = 4.4 Hz), 3.75 (s, 3H), 3.08 (t, 4H, J = 4.6 Hz), 2.47 (s, 3H), 1.38 (d, 6H, J = 6.0 Hz). |
| 27 | 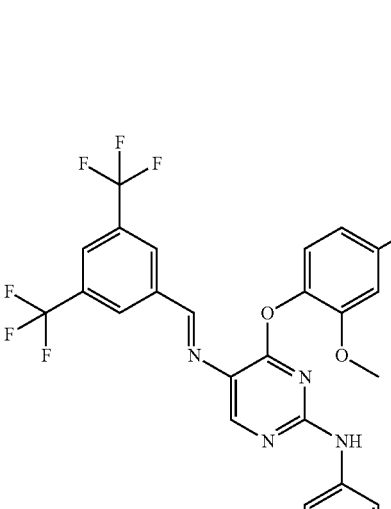 | 9.23 (s, 1H), 8.47 (s, 1H), 8.39 (s, 2H), 7.95 (s, 1H), 7.21 (d, 2H, J = 8.4 Hz), 7.11 (d, 1H, J = 7.8 Hz), 7.08 (s, 1H), 6.91-6.88 (m, 2H), 6.72 (d, 2H, J = 8.8 Hz), 3.89 (t, 4H, J = 4.6 Hz), 3.77 (s, 3H), 3.10 (t, 4H, J = 4.8 Hz), 2.49 (s, 3H). |

TABLE 2-continued

| Example | Compound structure | $^1$H NMR (ppm) δ |
|---|---|---|
| 28 | 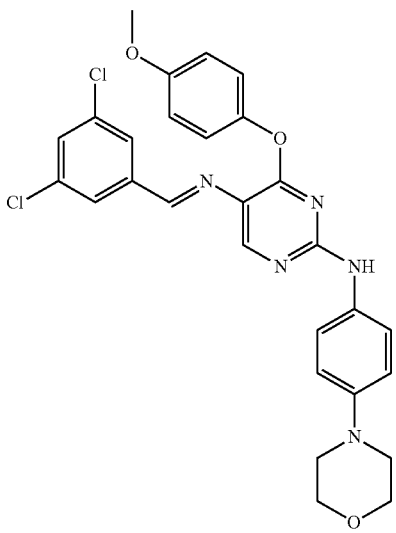 [SMILES: COc1ccc(Oc2nc(Nc3ccc(N4CCOCC4)cc3)ncc2/N=C/c2cc(Cl)cc(Cl)c2)cc1] | 8.89 (s, 1H), 8.33 (s, 1H), 7.80 (d, 2H, J = 1.9 Hz), 7.43 (t, 1H, J = 1.9 Hz), 7.21 (d, 2H, J = 8.4 Hz), 7.13 (d, 2H, J = 9.1 Hz), 7.00-6.98 (m, 3H), 6.72 (d, 2H, J = 8.6 Hz), 3.88-3.85 (m, 7H), 3.08 (t, 4H, J = 4.8 Hz). |

Example 29. Preparation of N5-(3,5-bis(trifluoromethyl)benzyl)-4-(2-methoxy-4-methylphenoxy)-N2-(4-morpholinophenyl)pyrimidine-2,5-diamine After dissolving 4-(2-methoxy-4-methylphenoxy)-N2-(4-morpholinophenyl)pyrimidine-2,5-diamine (0.08 g, 0.20 mmol) in 5 mL of anhydrous isopropanol and adding a catalytic amount of trifluoroacetic acid, 3,5-bis(trifluoromethyl)benzaldehyde (0.05 g, 0.22 mmol) was added. The reaction mixture was heated at 80° C. for 12 hours under reflux. After cooling the reaction mixture to room temperature and adding sodium cyanoborohydride (0.03 g, 0.40 mmol), the mixture was stirred at room temperature for 12 hours. After the reaction was completed, the reaction mixture was neutralized by adding triethylamine and a residue was obtained by concentrating under reduced pressure. The residue was purified by chromatography using a mixture of ethyl acetate and n-hexane as a mobile phase. The target compound was obtained with a yield of 54%.

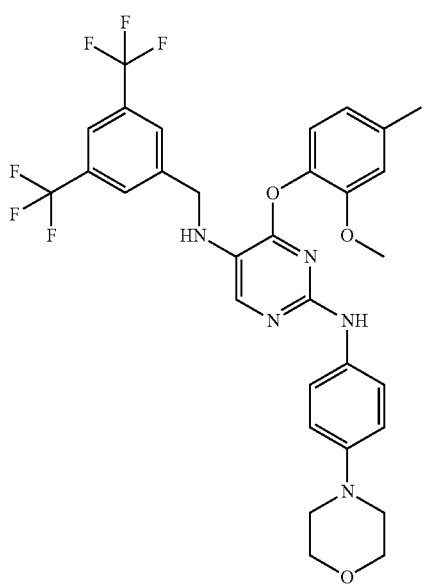 [SMILES: COc1cc(C)ccc1Oc1nc(Nc2ccc(N3CCOCC3)cc2)ncc1NCc1cc(C(F)(F)F)cc(C(F)(F)F)c1]

$^1$H NMR (400 MHz, CDCl$_3$) δ 7.89 (s, 2H), 7.80 (s, 1H), 7.51 (s, 1H), 7.25 (s, 1H), 7.18 (d, 2H, J=9.0 Hz), 7.07 (d, 1H, J=7.8 Hz), 6.85-6.83 (m, 2H), 6.70 (d, 2H, J=9.0 Hz), 6.59 (s, 1H), 4.50 (s, 2H), 4.31 (s, 1H), 3.83 (t, 4H, J=4.6 Hz), 3.73 (s, 3H), 3.02 (t, 4H, J=4.7 Hz), 2.43 (s, 3H).

6-Phenoxypyrimidine derivative compounds were synthesized in the same manner as in Example 29. Their structures and $^1$H NMR data are described in Table 3.

TABLE 3

| Example | Chemical structure | ¹H NMR (ppm) δ |
| --- | --- | --- |
| 30 | 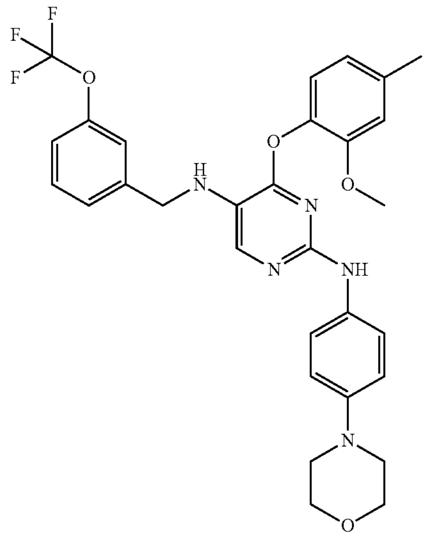 [SMILES: COc1cc(C)ccc1Oc1nc(Nc2ccc(N3CCOCC3)cc2)ncc1NCc1cccc(OC(F)(F)F)c1] | 7.57 (s, 1H), 7.40-7.34 (m, 2H), 7.28 (s, 1H), 7.18 (d, 2H, J = 8.9 Hz), 7.13 (d, 1H, J = 7.2 Hz), 7.05 (d, 1H, J = 7.8 Hz), 6.84-6.82 (m, 2H), 6.69 (d, 2H, J = 8.9 Hz), 6.62 (s, 1H), 4.41 (s, 2H), 3.84 (t, 4H, J = 4.6 Hz), 3.73 (s, 3H), 3.02 (t, 4H, J = 4.7 Hz), 2.43 (s, 3H). |
| 31 | 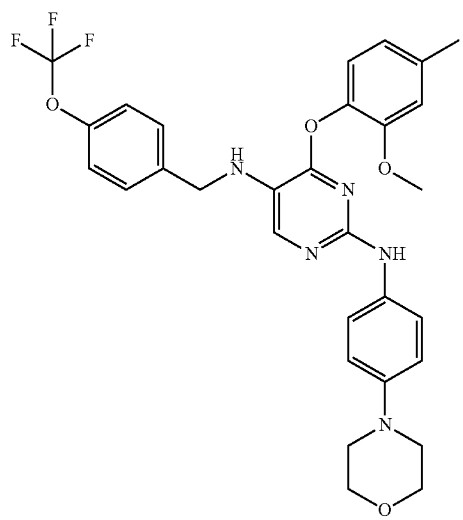 [SMILES: COc1cc(C)ccc1Oc1nc(Nc2ccc(N3CCOCC3)cc2)ncc1NCc1ccc(OC(F)(F)F)cc1] | 7.60 (s, 1H), 7.44 (d, 2H, J = 8.6 Hz), 7.21-7.17 (m, 4H), 7.04 (d, 1H, J = 7.8 Hz), 6.84-6.81 (m, 2H), 6.70 (d, 2H, J = 9.0 Hz), 6.49 (s, 1H), 4.38 (s, 2H), 4.18 (s, 1H), 3.84 (t, 4H, J = 4.6 Hz), 3.73 (s, 3H), 3.03 (t, 4H, J = 4.7 Hz), 2.42 (s, 3H). |
| 32 | 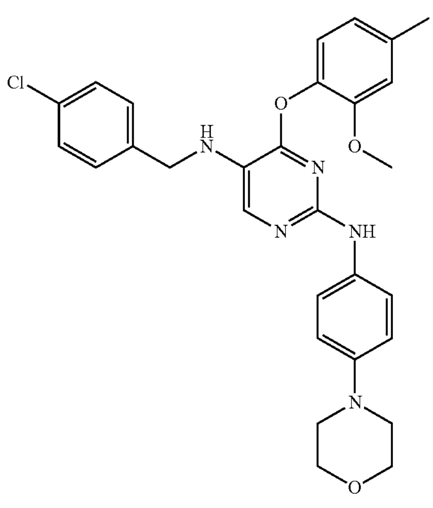 [SMILES: COc1cc(C)ccc1Oc1nc(Nc2ccc(N3CCOCC3)cc2)ncc1NCc1ccc(Cl)cc1] | 7.58 (s, 1H), 7.36-7.30 (m, 4H), 7.17 (d, 2H, J = 8.9 Hz), 7.04 (d, 1H, J = 7.8 Hz), 6.84-6.81 (m, 2H), 6.69 (d, 2H, J = 9.0 Hz), 6.60 (s, 1H), 4.35 (s, 2H), 3.84 (t, 4H, J = 4.7 Hz), 3.73 (s, 3H), 3.02 (t, 4H, J = 4.7 Hz), 2.43 (s, 3H). |

TABLE 3-continued

| Example | Chemical structure | $^1$H NMR (ppm) δ |
|---|---|---|
| 33 | 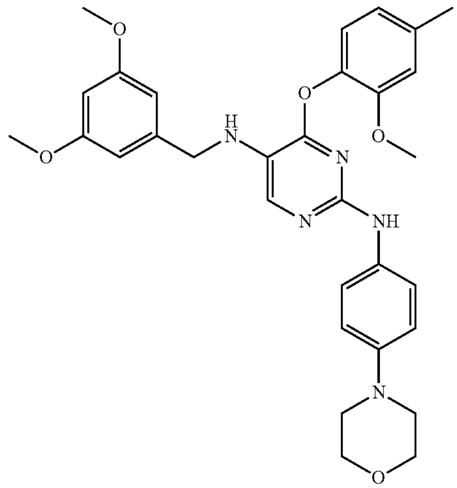 | 7.62 (s, 1H), 7.18 (d, 2H, J = 8.9 Hz), 7.04 (d, 1H, J = 7.8 Hz), 6.84-6.81 (m, 2H), 6.69 (d, 2H, J = 8.9 Hz), 6.58-6.57 (m, 3H), 6.37 (t, 1H, J = 1.9 Hz), 4.32 (s, 2H), 3.84 (t, 4H, J = 4.5 Hz), 3.79 (s, 6H), 3.73 (s, 3H), 3.02 (t, 4H, J = 4.6 Hz), 2.42 (s, 3H). |

The activity of the novel compounds represented by Chemical Formula 1 according to the present invention was investigated through test examples as described below.

TEST EXAMPLES

Test Example 1 Measurement of Cell Viability

RAW 264.7 macrophages were seeded onto a 24-well plate, cultured with a sample or an adequate positive control under various concentration conditions and then LPS (lipopolysaccharides) were activated for 24 hours. After adding a 20 μL MTT (5 mg/mL) solution to each well, the cells were cultured further for 4 hours. After removing the supernatant, 1 mL of formazan dissolved in dimethyl sulfoxide (DMSO) was added to each well. Then, absorbance was measured by ELISA at a wavelength of 540 nm.

FIG. 1 shows a result of measuring cell viability for (E)-5-((3,5-dimethoxybenzylidene)amino)-4-(4-methoxyphenoxy)-N-(4-morpholinop henyl)pyrimidin-2-amine (Example 21) as a representative compound of the present invention. It was confirmed that the compound of the present invention can be used safely because it showed little toxicity.

Test Example 2. Measurement of Nitrite

RAW 264.7 macrophages were seeded onto a 24-well plate, cultured with a sample or an adequate positive control under various concentration conditions and then LPS (lipopolysaccharides) were activated for 24 hours. The concentration of nitrite accumulated in the culture medium was measured by the Griess test as a measure of nitric oxide (NO) production. L-NIL was used as the positive control.

FIG. 2 shows a result of measuring the concentration of the produced nitric oxide (NO) for (E)-5-((3,5-dimethoxybenzylidene)amino)-4-(4-methoxyphenoxy)-N-(4-morpholinop henyl)pyrimidin-2-amine (Example 21) as a representative compound of the present invention. The compound of the present invention could inhibit LPS-induced NO production in a dose-dependent manner and showed 2 times higher inhibitory activity as compared to the positive control L-NIL.

Test Example 3. Measurement of PEG2

FIG. 3 shows a result of measuring PEG2 production for (E)-5-((3,5-dimethoxybenzylidene)amino)-4-(4-methoxyphenoxy)-N-(4-morpholinophenyl)pyrimidin-2-amine (Example 21) as a representative compound of the present invention. It was confirmed that the compound of the present invention can inhibit LPS-induced PEG2 production in a dose-dependent manner.

Test Example 4. Western Blotting

Western blotting was conducted to identify the mechanism of the NO and PGE2 production inhibiting activity of the compound of the present invention. The inhibition of iNOS and COX-2 protein production and mRNA upregulation was tested.

FIG. 4 shows a result of conducting western blotting for (E)-5-((3,5-dimethoxybenzylidene)amino)-4-(4-methoxyphenoxy)-N-(4-morpholinophenyl)pyrimidin-2-amine (Example 21) as a representative compound of the present invention. And, FIGS. 5A and 5B show results of measuring the iNOS mRNA expression level and the COX-2 mRNA expression level, respectively. It was confirmed that the compound of the present invention can inhibit LPS-induced upregulation of iNOS mRNA.

Test Example 5. Measurement of Cytokine Production Inhibiting Activity

The inhibitory activity for the proinflammatory cytokines TNF-α, IL-1β and IL-6 was tested for the compound of the present invention.

FIGS. 6A, 6B and 6C show results of measuring TNF-α, IL-1β and IL-6 cytokine, respectively, for (E)-5-((3,5-dimethoxybenzylidene)amino)-4-(4-methoxyphenoxy)-N-(4-morpholinophenyl)pyrimidin-2-amine (Example 21) as a representative compound of the present invention. And, FIGS. 7A and 7B show a result of measuring the TNF-α mRNA expression level and the IL-6 mRNA expression level, respectively. It was confirmed that the compound of the present invention can inhibit the production of TNF-α and IL-6 at a concentration of 12 μM.

What is claimed is:

1. A compound selected from a group consisting of a 6-phenoxypyrimidine derivative represented by Chemical Formula 1 and a pharmaceutically acceptable salt thereof:

[Chemical Formula 1]

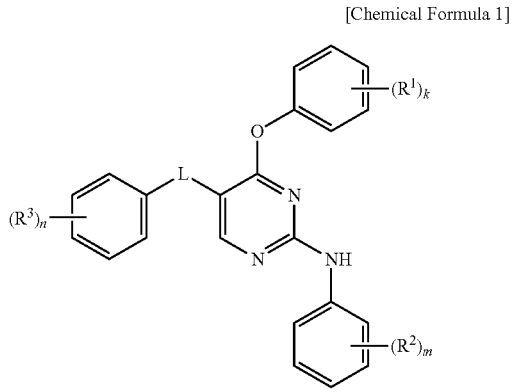

wherein

L is —C(O)NH—, —NHC(O)NH—, —CH=N— or —CH$_2$—NH—;

R$^1$ is a halogen atom, a C$_1$-C$_{10}$ alkyl group, a C$_1$-C$_{10}$ alkoxy group or a C$_1$-C$_{10}$ haloalkyl group substituted with 1-10 halogen atom(s);

R$^2$ is a morpholine group or a C$_1$-C$_{10}$ alkoxy group;

R$^3$ is a halogen atom, a C$_1$-C$_{10}$ alkyl group, a C$_1$-C$_{10}$ alkoxy group or a C$_1$-C$_{10}$ haloalkyl or C$_1$-C$_{10}$ haloalkoxy group substituted with 1-13 halogen atom(s); and k, m and n are integers from 0 to 3 as the number of substituents.

2. The compound according to claim 1,
wherein
the L is —C(O)NH—, —NHC(O)NH—, —CH=N— or —CH$_2$—NH—;

the R$^1$ is a halogen atom, a C$_1$-C$_6$ alkyl group, a C$_1$-C$_6$ alkoxy group or a C$_1$-C$_6$ haloalkyl group substituted with 1-10 halogen atom(s);

the R$^2$ is a morpholine group or a C$_1$-C$_6$ alkoxy group;

the R$^3$ is a halogen atom, a C$_1$-C$_6$ alkoxy group or a C$_1$-C$_6$ haloalkyl or C$_1$-C$_6$ haloalkoxy group substituted with 1-10 halogen atom(s); and the k, m and n are integers 1 or 2 as the number of substituents.

3. The compound according to claim 1, which is selected from a group consisting of a 6-phenoxypyrimidine derivative represented by Chemical Formula 1a and a pharmaceutically acceptable salt thereof:

[Chemical Formula 1a]

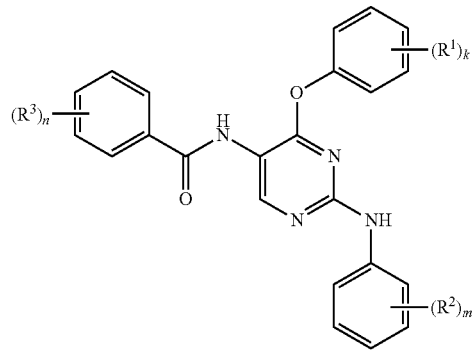

wherein

R$^1$ is a C$_1$-C$_6$ alkyl group or a C$_1$-C$_6$ alkoxy group;

R$^2$ is a morpholine group or a C$_1$-C$_6$ alkoxy group;

R$^3$ is a C$_1$-C$_6$ alkoxy group; and k, m and n are integers 1 or 2 as the number of substituents.

4. The compound according to claim 1, which is selected from a group consisting of 6-phenoxypyrimidine derivative represented by Chemical Formula 1b and a pharmaceutically acceptable salt thereof:

[Chemical Formula 1b]

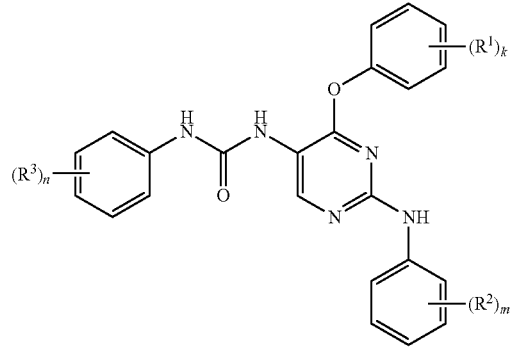

wherein

R$^1$ is a halogen atom, a C$_1$-C$_6$ alkyl group, a C$_1$-C$_6$ alkoxy group or a C$_1$-C$_6$ haloalkyl group substituted with 1-10 halogen atom(s);

R$^2$ is a morpholine group or a C$_1$-C$_6$ alkoxy group;

R$^3$ is a halogen atom, a C$_1$-C$_6$ alkoxy group or a C$_1$-C$_6$ haloalkyl group substituted with 1-10 halogen atom(s); and k, m and n are integers 1 or 2 as the number of substituents.

5. The compound according to claim 1, which is selected from a group consisting of a 6-phenoxypyrimidine derivative represented by Chemical Formula 1c and a pharmaceutically acceptable salt thereof:

[Chemical Formula 1c]

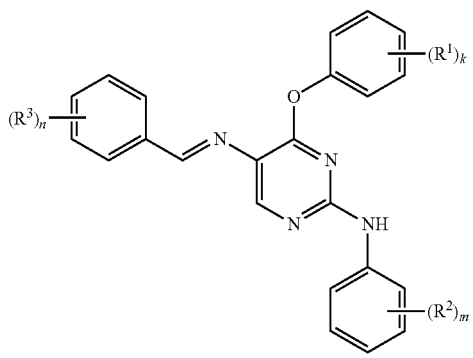

wherein
R¹ is a $C_1$-$C_6$ alkyl group or a $C_1$-$C_6$ alkoxy group;
R² is a morpholine group;
R³ is a halogen atom, a $C_1$-$C_6$ alkoxy group or a $C_1$-$C_6$ haloalkyl or $C_1$-$C_6$ haloalkoxy group substituted with 1-10 halogen atom(s); and
k, m and n are integers 1 or 2 as the number of substituents.

6. The compound according to claim 1, which is selected from a group consisting of a 6-phenoxypyrimidine derivative represented by Chemical Formula 1d and a pharmaceutically acceptable salt thereof:

[Chemical Formula 1d]

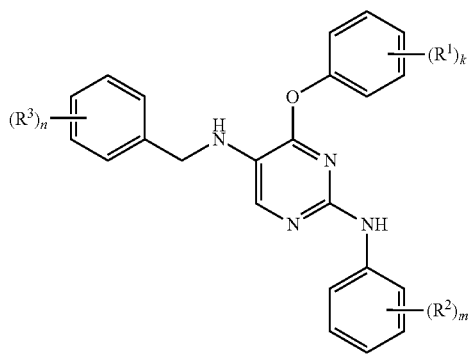

wherein
R¹ is a $C_1$-$C_6$ alkyl group or a $C_1$-$C_6$ alkoxy group;
R² is a morpholine group;
R³ is a halogen atom, a $C_1$-$C_6$ alkoxy group or a $C_1$-$C_6$ haloalkyl or $C_1$-$C_6$ haloalkoxy group substituted with 1-10 halogen atom(s); and
k, m and n are integers 1 or 2 as the number of substituents.

7. The compound according to claim 1, which is selected from a group consisting of:
1) N-(2-(3,5-dimethoxyphenylamino)-4-(2-methoxy-4-methylphenoxy)methylphenoxy)-3,5-dimethoxybenzamide;
2) 3,5-dimethoxy-N-(4-(2-methoxy-4-methylphenoxy)-2-(4-morpholinophenylamino)methylphenoxy)benzamide;
3) 1-(3,5-dimethoxyphenyl)-3-(2-(3,5-dimethoxyphenylamino)-4-(2-methoxy-4-methylphenoxy)methylphenoxy)urea;
4) 1-(3,5-dimethoxyphenyl)-3-(4-(2-methoxy-4-methylphenoxy)-2-(4-morpholinophenylamino)methylphenoxy)urea;
5) 1-(2-(3,5-dimethoxyphenylamino)-4-(2-methoxy-4-methylphenoxy)methylphenoxy)-3-(4-methoxyphenyl)urea;
6) 1-(2,6-dichlorophenyl)-3-(2-(3,5-dimethoxyphenylamino)-4-(2-methoxy-4-methylphenoxy)methylphenoxy)urea;
7) 1-(2,6-dichlorophenyl)-3-(4-(2-methoxy-4-methylphenoxy)-2-(4-morpholinophenylamino)methylphenoxy)urea;
8) 1-(3,5-dichlorophenyl)-3-(4-(2-methoxy-4-methylphenoxy)-2-((4-morpholinophenyl)amino)methylphenoxy)urea;
9) 1-(4-(2-methoxy-4-methylphenoxy)-2-((4-morpholinophenyl)amino)methylphenoxy)-3-(2-methoxyphenyl)urea;
10) 1-(3,5-dimethoxyphenyl)-3-(4-(3-methoxyphenoxy)-2-((4-morpholinophenyl)amino)methylphenoxy)urea;
11) 1-(3,5-dimethoxyphenyl)-3-(2-(4-morpholinophenylamino)-4-(4-(trifluoromethyl)phenoxy)methylphenoxy)urea;
12) 1-(3,5-dimethoxyphenyl)-3-(4-(4-fluorophenoxy)-2-(4-morpholinophenylamido)methylphenoxy)urea;
13) 1-(3,5-bistrifluoromethylphenyl)-3-(4-(2-methoxy-4-methylphenoxy)-2-((2-morpholinophenyl)amino)methylphenoxy)urea;
14) 1-(3,5-dichlorophenyl)-3-(4-(3-methoxyphenoxy)-2-((2-morpholinophenyl)amino)methylphenoxy)urea;
15) 1-(2,6-dichlorophenyl)-3-(4-(3-methoxyphenoxy)-2-((2-morpholinophenyl)amino)methylphenoxy)urea;
16) (E)-5-((3,5-dimethoxybenzylidene)amino)-4-(2-methoxy-4-methylphenoxy)-N-(4-morpholinophenyl)pyrimidin-2-amine;
17) (E)-5-((3,5-dimethoxybenzylidene)amino)-4-(3-methoxyphenoxy)-N-(4-morpholinophenyl)pyrimidin-2-amine;
18) (E)-5-((2-chlorobenzylidene)amino)-4-(2-methoxy-4-methylphenoxy-N-(4-morpholinophenyl)pyrimidin-2-amine;
19) (E)-5-((3-chlorobenzylidene)amino)-4-(2-methoxy-4-methylphenoxy-N-(4-morpholinophenyl)pyrimidin-2-amine;
20) (E)-4-(4-(trifluoromethyl)phenoxy)-N-(4-morpholinophenyl)-5-((3,5-dimethoxybenzylidene)amino)pyrimidin-2-amine;
21) (E)-5-((3,5-dimethoxybenzylidene)amino)-4-(4-methoxyphenoxy)-N-(4-morpholinophenyl)pyrimidin-2-amine;
22) (E)-5-((4-chlorobenzylidene)amino)-4-(2-methoxy-4-methylphenoxy)-N-(4-morpholinophenyl)pyrimidin-2-amine;
23) (E)-5-((3,5-dimethoxybenzylidene)amino)-4-(4-fluorophenoxy)-N-(4-morpholinophenyl)pyrimidin-2-amine;
24) (E)-4-(2-methoxy-4-methylphenoxy)-N-(4-morpholinophenyl)-5-((3,5-dichlorobenzylidene)amino)pyrimidin-2-amine;
25) (E)-4-(2-methoxy-4-methylphenoxy)-N-(4-morpholinophenyl)-5-((3-(trifluoromethoxy)benzylidene)amino)pyrimidin-2-amine;
26) (E)-5-((3-isopropoxybenzylidene)amino)-4-(2-methoxy-4-methylphenoxy)-N-(4-morpholinophenyl)pyrimidin-2-amine;

27) (E)-5-((3,5-bis(trifluoromethyl)benzylidene)amino-4-(2-methoxy-4-methylphenoxy)-N-(4-morpholinophenyl)pyrimidin-2-amine;
28) (E)-5-((3,5-dichlorobenzylidene)amino)-4-(4-methoxyphenoxy)-N-(4-morpholinophenyl)pyrimidin-2-amine;
29) N5-(3,5-bis(trifluoromethyl)benzyl)-4-(2-methoxy-4-methylphenoxy)-N2-(4-morpholinophenyl)pyrimidine-2,5-diamine;
30) 4-(2-methoxy-4-methylphenoxy)-N2-(4-morpholinophenyl)-N5-(3-(trifluoro)benzyl)pyrimidine-2,5-diamine;
31) 4-(2-methoxy-4-methylphenoxy)-N2-(morpholinophenyl)-N4-(4-(trifluoromethoxy)benzyl)pyrimidine-2,5-diamine;
32) N4-(4-chlorobenzyl)-4-(2-methoxy-4-methylphenoxy)-N2-(4-morpholinophenyl)pyrimidine-2,5-diamine;
33) N5-(3,5-dimethoxybenzyl)-4-(2-methoxy-4-methylphenoxy)-N2-(4-morpholinophenyl)pyrimidine-2,5-diamine; and
a pharmaceutically acceptable salt thereof.

8. A method for treating or ameliorating an inflammatory disease of a subject, wherein the method comprises administering an effective amount of the compound according to claim 1 to the subject in need thereof.

9. The method according to claim 8, wherein the inflammatory disease is selected from a group consisting of rheumatoid arthritis, psoriatic arthritis, inflammatory bowel disease and Crohn's disease.

10. A method for preparing the compound according to claim 1, comprising:
(step a) a step of preparing a compound represented by Chemical Formula 4 by reacting 2,4-dichloro-5-nitropyrimidine represented by Chemical Formula 2 with a phenol compound represented by Chemical Formula 3;
(step b) a step of preparing a compound represented by Chemical Formula 6 by reacting the compound represented by Chemical Formula 4 with an aniline derivative represented by Chemical Formula 5; and
(step c) a step of preparing an amine compound represented by Chemical Formula 7 by reducing the nitro compound represented by Chemical Formula 6, Chemical Formula 2

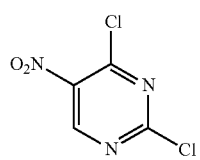

Chemical Formula 3

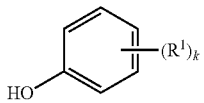

Chemical Formula 4

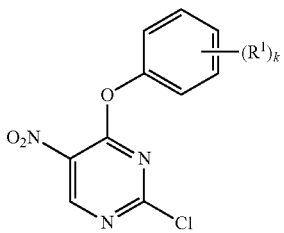

Chemical Formula 5

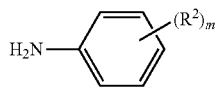

Chemical Formula 6

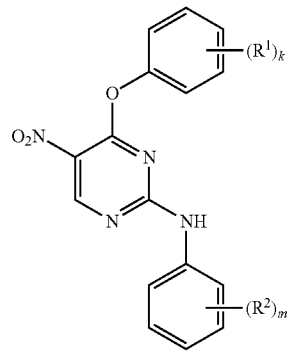

Chemical Formula 7

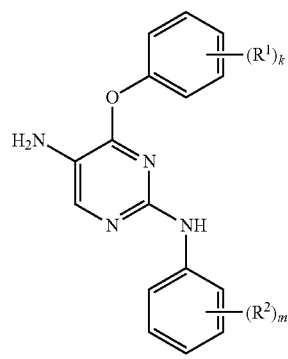

wherein R1, R2, k and m are the same as defined in claim 1.

11. The method according to claim 10, comprising:
(step a) a step of preparing a compound represented by Chemical Formula 4 by reacting 2,4-dichloro-5-nitropyrimidine represented by Chemical Formula 2 with a phenol compound represented by Chemical Formula 3;
(step b) a step of preparing a compound represented by Chemical Formula 6 by reacting the compound represented by Chemical Formula 4 with an aniline derivative represented by Chemical Formula 5;
(step c) a step of preparing an amine compound represented by Chemical Formula 7 by reducing the nitro compound represented by Chemical Formula 6; and
(step d-1) a step of preparing a compound represented by Chemical Formula 1a by reacting the amine compound represented by Chemical Formula 7 with an acid chloride derivative represented by Chemical Formula 8-1:

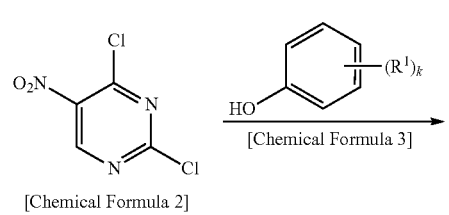

-continued

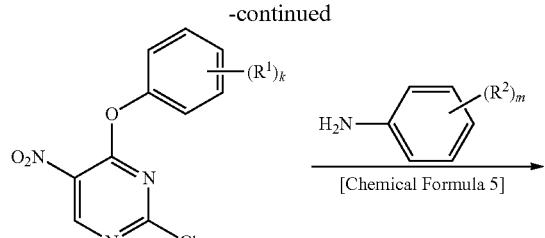

[Chemical Formula 4]

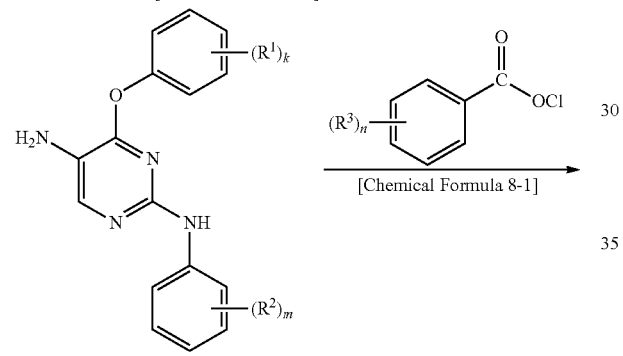

[Chemical Formula 6]

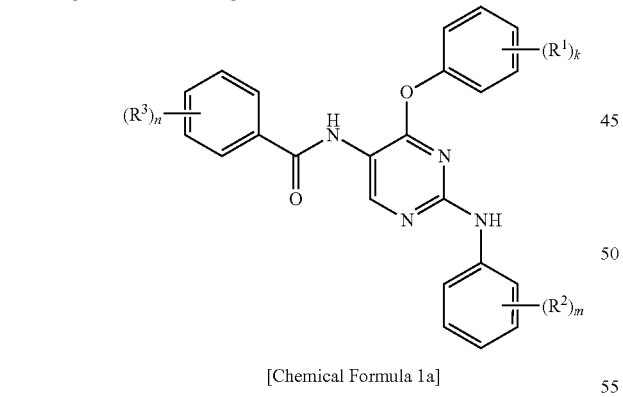

[Chemical Formula 7]

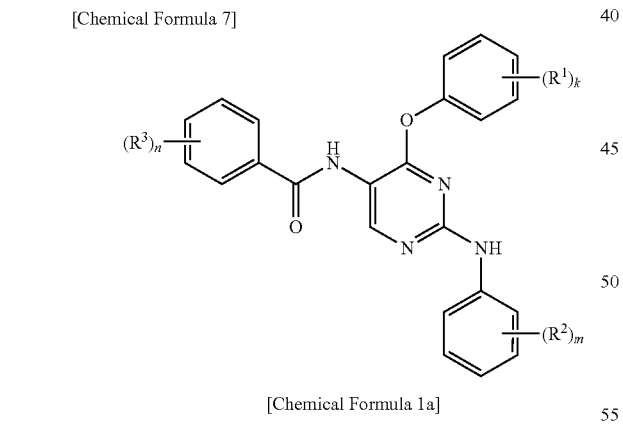

[Chemical Formula 1a]

wherein R¹, R², R³, k, m and n are the same as defined in claim 1.

12. The method according to claim 10, comprising:
(step a) a step of preparing a compound represented by Chemical Formula 4 by reacting 2,4-dichloro-5-nitropyrimidine represented by Chemical Formula 2 with a phenol compound represented by Chemical Formula 3;
(step b) a step of preparing a compound represented by Chemical Formula 6 by reacting the compound represented by Chemical Formula 4 with an aniline derivative represented by Chemical Formula 5;

(step c) a step of preparing an amine compound represented by Chemical Formula 7 by reducing the nitro compound represented by Chemical Formula 6; and (step d-2) a step of preparing a compound represented by Chemical Formula 1b by reacting the amine compound represented by Chemical Formula 7 with an isocyanate derivative represented by Chemical Formula 8-2:

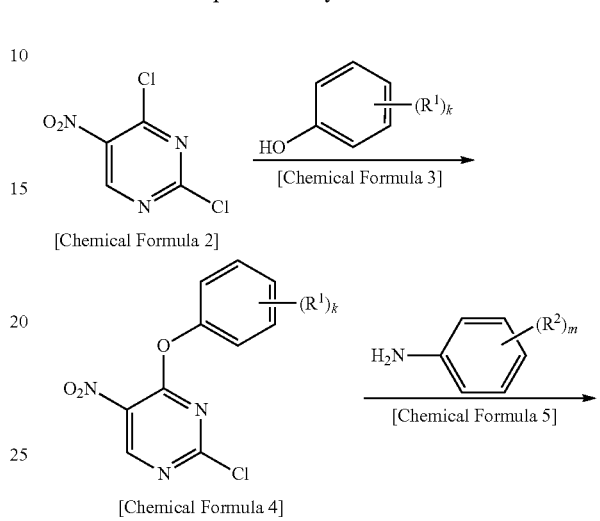

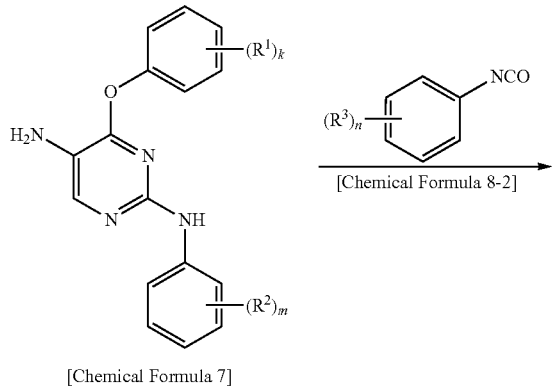

[Chemical Formula 7]

-continued

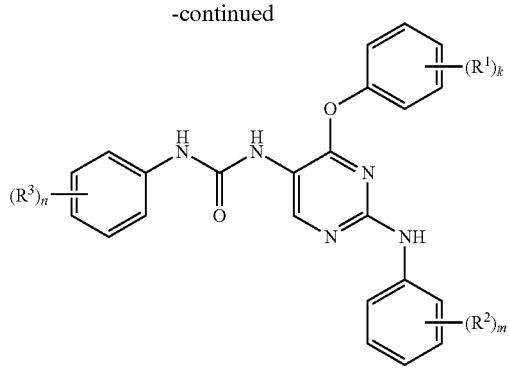

[Chemical Formula 1b]

wherein $R^1$, $R^2$, $R^3$, k, m and n are the same as defined in claim 1.

13. The method according to claim 10, comprising:
(step a) a step of preparing a compound represented by Chemical Formula 4 by reacting 2,4-dichloro-5-nitropyrimidine represented by Chemical Formula 2 with a phenol compound represented by Chemical Formula 3;
(step b) a step of preparing a compound represented by Chemical Formula 6 by reacting the compound represented by Chemical Formula 4 with an aniline derivative represented by Chemical Formula 5;
(step c) a step of preparing an amine compound represented by Chemical Formula 7 by reducing the nitro compound represented by Chemical Formula 6; and
(step d-3) a step of preparing a compound represented by Chemical Formula 1c by reacting the amine compound represented by Chemical Formula 7 with an aldehyde derivative represented by Chemical Formula 8-3:

-continued

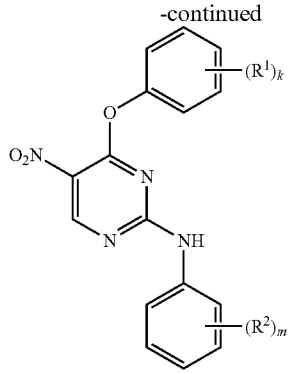

[Chemical Formula 6]

[Chemical Formula 7]

[Chemical Formula 1c]

wherein $R^1$, $R^2$, $R^3$, k, m and n are the same as defined in claim 1.

14. The method according to claim 10, comprising:
(step a) a step of preparing a compound represented by Chemical Formula 4 by reacting 2,4-dichloro-5-nitropyrimidine represented by Chemical Formula 2 with a phenol compound represented by Chemical Formula 3;
(step b) a step of preparing a compound represented by Chemical Formula 6 by reacting the compound represented by Chemical Formula 4 with an aniline derivative represented by Chemical Formula 5;
(step c) a step of preparing an amine compound represented by Chemical Formula 7 by reducing the nitro compound represented by Chemical Formula 6; and
(step d-4) a step of preparing a compound represented by Chemical Formula 1d by reacting the amine compound represented by Chemical Formula 7 with an aldehyde derivative represented by Chemical Formula 8-3 and then reducing the product:

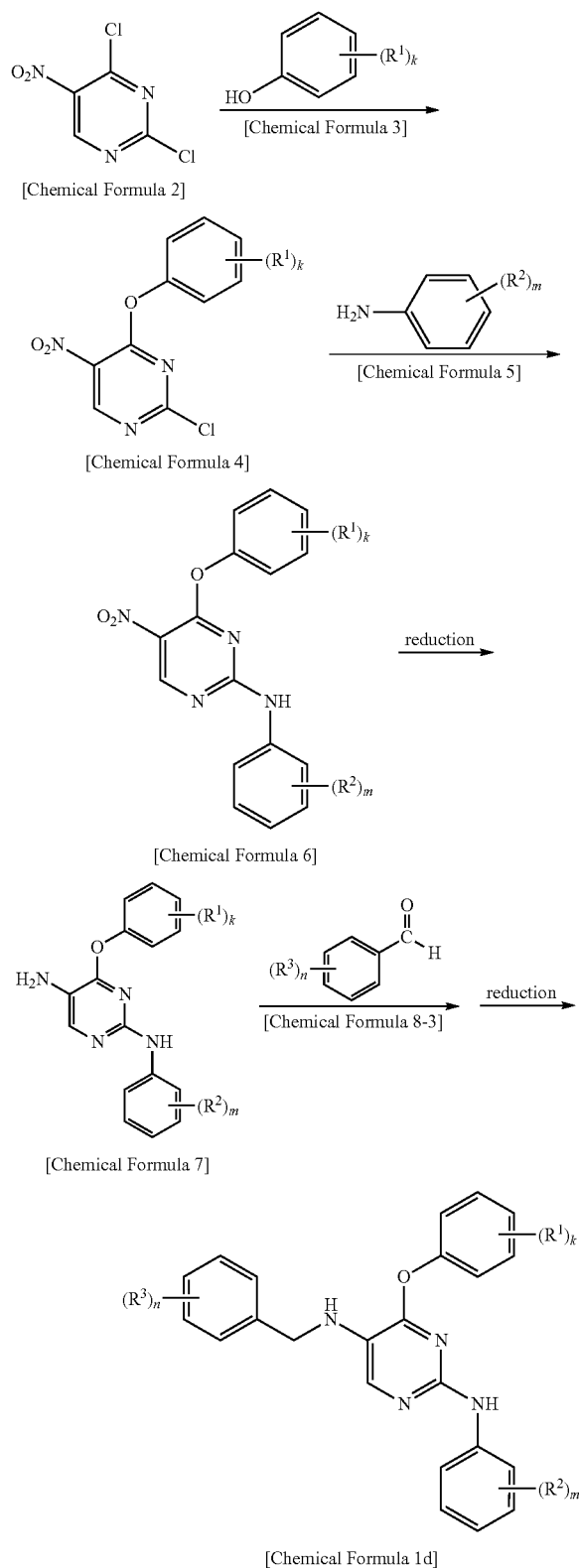

wherein $R^1$, $R^2$, $R^3$, k, m and n are the same as defined in claim 1.

15. The method according to claim 8, wherein the compound is selected from a group consisting of:

1) N-(2-(3,5-dimethoxyphenylamino)-4-(2-methoxy-4-methylphenoxy)methylphenoxy)-3,5-dimethoxybenzamide;
2) 3,5-dimethoxy-N-(4-(2-methoxy-4-methylphenoxy)-2-(4-morpholinophenylamino)methylphenoxy)benzamide;
3) 1-(3,5-dimethoxyphenyl)-3-(2-(3,5-dimethoxyphenylamino)-4-(2-methoxy-4-methylphenoxy)methylphenoxy)urea;
4) 1-(3,5-dimethoxyphenyl)-3-(4-(2-methoxy-4-methylphenoxy)-2-(4-morpholinophenylamino)methylphenoxy)urea;
5) 1-(2-(3,5-dimethoxyphenylamino)-4-(2-methoxy-4-methylphenoxy)methylphenoxy)-3-(4-methoxyphenyl)urea;
6) 1-(2,6-dichlorophenyl)-3-(2-(3,5-dimethoxyphenylamino)-4-(2-methoxy-4-methylphenoxy)methylphenoxy)urea;
7) 1-(2,6-dichlorophenyl)-3-(4-(2-methoxy-4-methylphenoxy)-2-(4-morpholinophenylamino)methylphenoxy)urea;
8) 1-(3,5-dichlorophenyl)-3-(4-(2-methoxy-4-methylphenoxy)-2-((4-morpholinophenyl)amino)methylphenoxy)urea;
9) 1-(4-(2-methoxy-4-methylphenoxy)-2-((4-morpholinophenyl)amino)methylphenoxy)-3-(2-methoxyphenyl)urea;
10) 1-(3,5-dimethoxyphenyl)-3-(4-(3-methoxyphenoxy)-2-((4-morpholinophenyl)amino)methylphenoxy)urea;
11) 1-(3,5-dimethoxyphenyl)-3-(2-(4-morpholinophenylamino)-4-(4-(trifluoromethyl)phenoxy)methylphenoxy)urea;
12) 1-(3,5-dimethoxyphenyl)-3-(4-(4-fluorophenoxy)-2-(4-morpholinophenylamido)methylphenoxy)urea;
13) 1-(3,5-bistrifluoromethylphenyl)-3-(4-(2-methoxy-4-methylphenoxy)-2-((2-morpholinophenyl)amino)methylphenoxy)urea;
14) 1-(3,5-dichlorophenyl)-3-(4-(3-methoxyphenoxy)-2-((2-morpholinophenyl)amino)methylphenoxy)urea;
15) 1-(2,6-dichlorophenyl)-3-(4-(3-methoxyphenoxy)-2-((2-morpholinophenyl)amino)methylphenoxy)urea;
16) (E)-5-((3,5-dimethoxybenzylidene)amino)-4-(2-methoxy-4-methylphenoxy)-N-(4-morpholinophenyl)pyrimidin-2-amine;
17) (E)-5-((3,5-dimethoxybenzylidene)amino)-4-(3-methoxyphenoxy)-N-(4-morpholinophenyl)pyrimidin-2-amine;
18) (E)-5-((2-chlorobenzylidene)amino)-4-(2-methoxy-4-methylphenoxy-N-(4-morpholinophenyl)pyrimidin-2-amine;
19) (E)-5-((3-chlorobenzylidene)amino)-4-(2-methoxy-4-methylphenoxy-N-(4-morpholinophenyl)pyrimidin-2-amine;
20) (E)-4-(4-(trifluoromethyl)phenoxy)-N-(4-morpholinophenyl)-5-((3,5-dimethoxybenzylidene)amino)pyrimidin-2-amine;
21) (E)-5-((3,5-dimethoxybenzylidene)amino)-4-(4-methoxyphenoxy)-N-(4-morpholinophenyl)pyrimidin-2-amine;
22) (E)-5-((4-chlorobenzylidene)amino)-4-(2-methoxy-4-methylphenoxy)-N-(4-morpholinophenyl)pyrimidin-2-amine;
23) (E)-5-((3,5-dimethoxybenzylidene)amino)-4-(4-fluorophenoxy)-N-(4-morpholinophenyl)pyrimidin-2-amine;

24) (E)-4-(2-methoxy-4-methylphenoxy)-N-(4-morpholinophenyl)-5-((3,5-dichlorobenzylidene)amino)pyrimidin-2-amine;
25) (E)-4-(2-methoxy-4-methylphenoxy)-N-(4-morpholinophenyl)-5-((3-(trifluoromethoxy)benzylidene)amino)pyrimidin-2-amine;
26) (E)-5-((3-isopropoxybenzylidene)amino)-4-(2-methoxy-4-methylphenoxy)-N-(4-morpholinophenyl)pyrimidin-2-amine;
27) (E)-5-((3,5-bis(trifluoromethyl)benzylidene)amino-4-(2-methoxy-4-methylphenoxy)-N-(4-morpholinophenyl)pyrimidin-2-amine;
28) (E)-5-((3,5-dichlorobenzylidene)amino)-4-(4-methoxyphenoxy)-N-(4-morpholinophenyl)pyrimidin-2-amine;
29) N5-(3,5-bis(trifluoromethyl)benzyl)-4-(2-methoxy-4-methylphenoxy)-N2-(4-morpholinophenyl)pyrimidine-2,5-diamine;
30) 4-(2-methoxy-4-methylphenoxy)-N2-(4-morpholinophenyl)-N5-(3-(trifluoro)benzyl)pyrimidine-2,5-diamine;
31) 4-(2-methoxy-4-methylphenoxy)-N2-(morpholinophenyl)-N4-(4-(trifluoromethoxy)benzyl)pyrimidine-2,5-diamine;
32) N4-(4-chlorobenzyl)-4-(2-methoxy-4-methylphenoxy)-N2-(4-morpholinophenyl)pyrimidine-2,5-diamine;
33) N5-(3,5-dimethoxybenzyl)-4-(2-methoxy-4-methylphenoxy)-N2-(4-morpholinophenyl)pyrimidine-2,5-diamine; and
a pharmaceutically acceptable salt thereof.

16. The method according to claim 10, wherein the compound is selected from a group consisting of:
1) N-(2-(3,5-dimethoxyphenylamino)-4-(2-methoxy-4-methylphenoxy)methylphenoxy)-3,5-dimethoxybenzamide;
2) 3,5-dimethoxy-N-(4-(2-methoxy-4-methylphenoxy)-2-(4-morpholinophenylamino)methylphenoxy)benzamide;
3) 1-(3,5-dimethoxyphenyl)-3-(2-(3,5-dimethoxyphenylamino)-4-(2-methoxy-4-methylphenoxy)methylphenoxy)urea;
4) 1-(3,5-dimethoxyphenyl)-3-(4-(2-methoxy-4-methylphenoxy)-2-(4-morpholinophenylamino)methylphenoxy)urea;
5) 1-(2-(3,5-dimethoxyphenylamino)-4-(2-methoxy-4-methylphenoxy)methylphenoxy)-3-(4-methoxyphenyl)urea;
6) 1-(2,6-dichlorophenyl)-3-(2-(3,5-dimethoxyphenylamino)-4-(2-methoxy-4-methylphenoxy)methylphenoxy)urea;
7) 1-(2,6-dichlorophenyl)-3-(4-(2-methoxy-4-methylphenoxy)-2-(4-morpholinophenylamino)methylphenoxy)urea;
8) 1-(3,5-dichlorophenyl)-3-(4-(2-methoxy-4-methylphenoxy)-2-((4-morpholinophenyl)amino)methylphenoxy)urea;
9) 1-(4-(2-methoxy-4-methylphenoxy)-2-((4-morpholinophenyl)amino)methylphenoxy)-3-(2-methoxyphenyl)urea;
10) 1-(3,5-dimethoxyphenyl)-3-(4-(3-methoxyphenoxy)-2-((4-morpholinophenyl)amino)methylphenoxy)urea;
11) 1-(3,5-dimethoxyphenyl)-3-(2-(4-morpholinophenylamino)-4-(4-(trifluoromethyl)phenoxy)methylphenoxy)urea;
12) 1-(3,5-dimethoxyphenyl)-3-(4-(4-fluorophenoxy)-2-(4-morpholinophenylamido)methylphenoxy)urea;
13) 1-(3,5-bistrifluoromethylphenyl)-3-(4-(2-methoxy-4-methylphenoxy)-2-((2-morpholinophenyl)amino)methylphenoxy)urea;
14) 1-(3,5-dichlorophenyl)-3-(4-(3-methoxyphenoxy)-2-((2-morpholinophenyl)amino)methylphenoxy)urea;
15) 1-(2,6-dichlorophenyl)-3-(4-(3-methoxyphenoxy)-2-((2-morpholinophenyl)amino)methylphenoxy)urea;
16) (E)-5-((3,5-dimethoxybenzylidene)amino)-4-(2-methoxy-4-methylphenoxy)-N-(4-morpholinophenyl)pyrimidin-2-amine;
17) (E)-5-((3,5-dimethoxybenzylidene)amino)-4-(3-methoxyphenoxy)-N-(4-morpholinophenyl)pyrimidin-2-amine;
18) (E)-5-((2-chlorobenzylidene)amino)-4-(2-methoxy-4-methylphenoxy-N-(4-morpholinophenyl)pyrimidin-2-amine;
19) (E)-5-((3-chlorobenzylidene)amino)-4-(2-methoxy-4-methylphenoxy)-N-(4-morpholinophenyl)pyrimidin-2-amine;
20) (E)-4-(4-(trifluoromethyl)phenoxy)-N-(4-morpholinophenyl)-5-((3,5-dimethoxybenzylidene)amino)pyrimidin-2-amine;
21) (E)-5-((3,5-dimethoxybenzylidene)amino)-4-(4-methoxyphenoxy)-N-(4-morpholinophenyl)pyrimidin-2-amine;
22) (E)-5-((4-chlorobenzylidene)amino)-4-(2-methoxy-4-methylphenoxy)-N-(4-morpholinophenyl)pyrimidin-2-amine;
23) (E)-5-((3,5-dimethoxybenzylidene)amino)-4-(4-fluorophenoxy)-N-(4-morpholinophenyl)pyrimidin-2-amine;
24) (E)-4-(2-methoxy-4-methylphenoxy)-N-(4-morpholinophenyl)-5-((3,5-dichlorobenzylidene)amino)pyrimidin-2-amine;
25) (E)-4-(2-methoxy-4-methylphenoxy)-N-(4-morpholinophenyl)-5-((3-(trifluoromethoxy)benzylidene)amino)pyrimidin-2-amine;
26) (E)-5-((3-isopropoxybenzylidene)amino)-4-(2-methoxy-4-methylphenoxy)-N-(4-morpholinophenyl)pyrimidin-2-amine;
27) (E)-5-((3,5-bis(trifluoromethyl)benzylidene)amino-4-(2-methoxy-4-methylphenoxy)-N-(4-morpholinophenyl)pyrimidin-2-amine;
28) (E)-5-((3,5-dichlorobenzylidene)amino)-4-(4-methoxyphenoxy)-N-(4-morpholinophenyl)pyrimidin-2-amine;
29) N5-(3,5-bis(trifluoromethyl)benzyl)-4-(2-methoxy-4-methylphenoxy)-N2-(4-morpholinophenyl)pyrimidine-2,5-diamine;
30) 4-(2-methoxy-4-methylphenoxy)-N2-(4-morpholinophenyl)-N5-(3-(trifluoro)benzyl)pyrimidine-2,5-diamine;
31) 4-(2-methoxy-4-methylphenoxy)-N2-(morpholinophenyl)-N4-(4-(trifluoromethoxy)benzyl)pyrimidine-2,5-diamine;
32) N4-(4-chlorobenzyl)-4-(2-methoxy-4-methylphenoxy)-N2-(4-morpholinophenyl)pyrimidine-2,5-diamine;
33) N5-(3,5-dimethoxybenzyl)-4-(2-methoxy-4-methylphenoxy)-N2-(4-morpholinophenyl)pyrimidine-2,5-diamine; and
a pharmaceutically acceptable salt thereof.

* * * * *